United States Patent [19]

Bou-Ghannam et al.

[11] Patent Number: 5,710,631

[45] Date of Patent: Jan. 20, 1998

[54] APPARATUS AND METHOD FOR STORING INTERFEROMETRIC IMAGES OF SCANNED DEFECTS AND FOR SUBSEQUENT STATIC ANALYSIS OF SUCH DEFECTS

[75] Inventors: Akram Aref Bou-Ghannam; Alan David Dorundo, both of Boca Raton; Michael Gerard Lisanke, Boynton Beach; Huizong Lu, Coconut Creek; Lanphuong Thi Pena, Ft. Lauderdale; Ali Reza Taheri, West Palm Beach, all of Fla.; Samuel Sheung-Lok So, San Jose, Calif.; Kenneth Wayne Watts, Boca Raton, Fla.; Darell Smith Whitaker, Essex Junction, Vt.

[73] Assignee: International Business Machines Corporation, Armonk, N.Y.

[21] Appl. No.: 789,031

[22] Filed: Jan. 27, 1997

Related U.S. Application Data

[63] Continuation of Ser. No. 426,778, Apr. 11, 1995, abandoned.

[51] Int. Cl.[6] ............................................. G01B 9/02
[52] U.S. Cl. .................................... 356/351; 356/359
[58] Field of Search ................................ 356/359, 360, 356/351, 357, 353, 354

[56] References Cited

U.S. PATENT DOCUMENTS 5,469,259 11/1995 Golby et al. ........................ 356/351

*Primary Examiner*—Frank G. Font
*Assistant Examiner*—Amanda Merlino
*Attorney, Agent, or Firm*—Richard A. Tomlin; Ronald V. Davidge

[57] ABSTRACT

An interferometer is used to locate and examine defects in a test surface of a test specimen. Defects are first located as the test surface is driven past the objective of the interferometer at a constant speed, with a darkfield interferogram being examined as it flows across a row of CCD elements. During this process, the location of each defect is stored. Next, the test specimen is sequentially moved into the locations at which static measurements are made using an area array of CCD elements. During these measurements, the phase angle relationship of the interferometer is varied so that heights of surface segments may be calculated. If some to these segments are located more than a quarter wave length of the interferometer light source from the surface at which the darkfield is established, a process is used to perform height corrections for segments within transition boundaries.

17 Claims, 21 Drawing Sheets

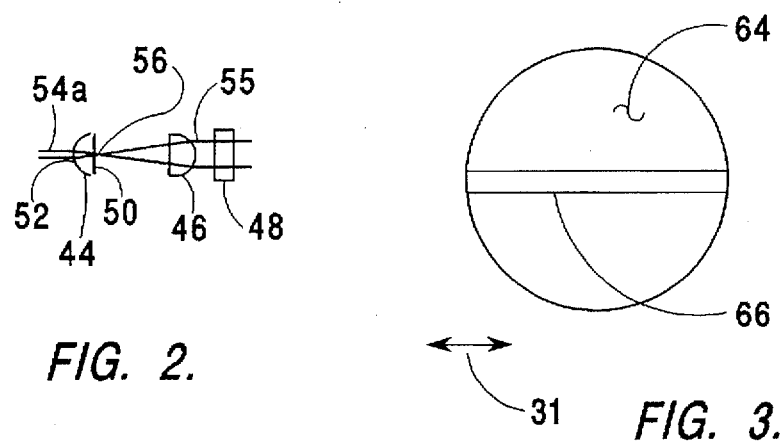
FIG. 2.
FIG. 3.
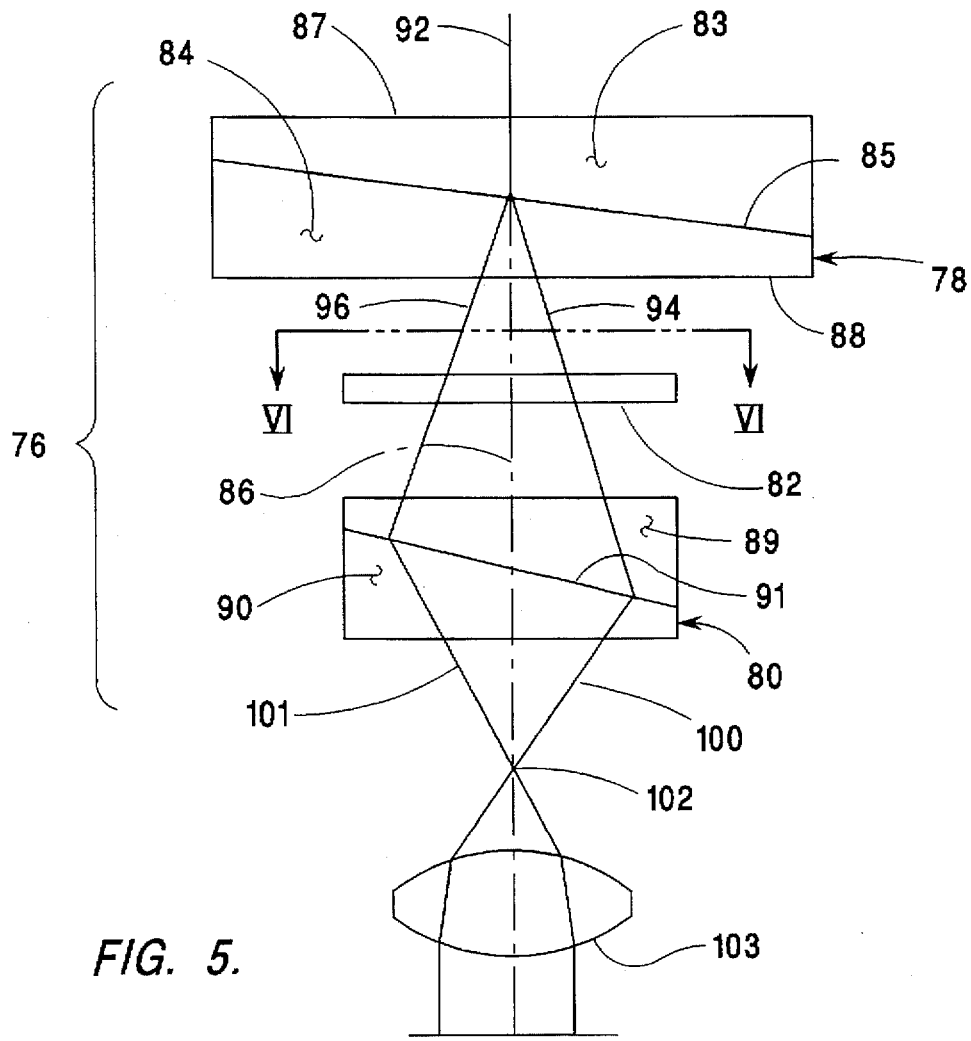
FIG. 5.

| FIGURE 30A. | FIGURE 30B. |
| FIGURE 30C. | FIGURE 30D. |

APPARATUS AND METHOD FOR STORING INTERFEROMETRIC IMAGES OF SCANNED DEFECTS AND FOR SUBSEQUENT STATIC ANALYSIS OF SUCH DEFECTS

CROSS REFERENCES TO RELATED APPLICATIONS

This is a continuation of application Ser. No. 08/426,778, filed Apr. 11 1995, now abandoned.

An application filed Jan. 3, 1994, copending with application Ser. No. 08/426,778 and issued as U.S. Pat. No. 5,469,259, to John. A. Golby, et al, having a common assignee with the present invention, describes an interferometer having a first light path directing an interferometric image to a line of sensing elements and a second light path directing such an image to an area army of sensing elements. The line of sensing elements is used as a surface being inspected is moved past the objective lens of the interferometer, and the area army of sensing elements is used as the surface is held in place at the objective lens.

BACKGROUND OF THE INVENTION

1. Field of the Invention

This invention relates to the acquisition and analysis of interferometric images and, more particularly, to the location of defects using a moving images scan followed by an analysis using static images.

2. Background Information

A surface profile interferometer is a device for determining the roughness of a surface or the height of a step change in the thickness of a part being measured. Such a step change may be caused, for example, by the application of a metal film to a substrate in the manufacture of a printed circuit board or an integrated micro-circuit. In general terms, an interferometer is an optical instrument in which two beams of light derived from the same monochromatic source are directed along optical paths of different length, in which the difference in length determines the nature of an interference pattern produced when the light beams are allowed to interfere. Since the beams of light are derived from the same monochromatic source, they are identical in wavelength. At equal path distances from the source, they are also in phase with one another. Phase differences between the beams therefore result only from differences in path length.

The phenomenon of light wave interference results from the mutual effect of two or more waves passing through the same region at the same time, producing reinforcement at some points and neutralization at other points, according to the principle of superposition.

With a photoelectric shearing interferometer, the height of a step change in a test surface may be measured using polarized light passed through a slit, through a Wollaston prism, and through a microscope objective lens, to form two images of the slit, with one image on each side of the step change. The beams reflected by the test surface pass through the lens and the prism, with an image being formed by two orthoganally polarized beams. The phase difference between these beams, which is determined by the height of the step, may be measured by the linear movement of a weak lens in a lateral direction (transverse to the beam) until the phase difference is exactly cancelled, as determined by the use of an electro-optic modulator, an analyzer, a photomultiplier, and a phase-sensitive detector, which are used together to detect the phase equality of the two interfering beams. The accuracy of the system depends on the precision to which the linear movement of the weak lens can be measured. Thus, a difference in phase between two orthogonal polarizations is measured, with the beams laterally displaced by the Wollaston prism, so that the system is not a common-path interferometer.

The Wollaston prism makes use of the phenomenon of double refraction or birefringence, through which a crystal of a transparent anisotropic material refracts orthogonally polarized light beams at different angles. Crystals such as calcite, quartz, and mica exhibit this property. A Wollaston prism includes two wedge-shaped segments held together with adjacent polished surfaces extending along a plane at an oblique angle to the optical axis of the device. The outer surfaces of the Wollaston prism lie along planes perpendicular to the optical axis of the device. The two segments of the Wollaston prism are composed of a birefringent material, with the crystal axes of the material lying perpendicular to each other and to the optical axis of the device.

For example, if a beam of light consisting of two sub-beams polarized orthogonally to each other is directed along the optical axis of the device to a Wollaston prism, the two beams will not be refracted at the initial surface of the prism, since it lies perpendicular to the direction of both beams. However, when the two beams reach the oblique surfaces inner surfaces of the two segments of the prism, refraction will occur, with the two beams being refracted at different angles because of the birefringence of the material of which the prism segments are composed. When the two beams reach the opposite external side of the prism, they are again refracted.

While the above discussion describes a Wollaston prism comprising two wedges of birefringent material, it is possible and often advantageous to form a prism of this kind using three or more such wedges, joined at two or more oblique planes. When this is done, the outer surfaces of the prism remain perpendicular to the optical center of the device.

Thus, a number of methods have been developed for using interferometers to provide accurate measurements of very small surface features. However, since these methods are based on rather elaborate and painstaking processes in which a very small surface area is held in place to be viewed through an interferometer, they are difficult to apply to the materials of a mass production process making, in large volumes, parts which would benefit from inspection by means of interferometry. What is needed, for example, is a way to apply a scanning process allowing a relatively large test surface to be checked without stopping for the measurement of individual areas. Such a process could then be applied, for example, to disks used for data storage.

With the device described in U.S. Pat. No. 5,469,259, what is needed is an automated method for using the relatively fast process of scanning a test surface while defect location data is accumulated form the line of photosensitive elements, followed by using the relatively thorough process of statically examining defects found in this way to calculate the heights of various defects, even when their surfaces extend more than a quarter wave-length, of the light used in the interferometer laser, from the average surface, used to maintain darkfield conditions, of the sample being tested.

DESCRIPTION OF THE PRIOR ART

U.S. Pat. No. 3,849,003 to Velzel describes an interferometer for measuring the roughness of a surface, including an optical system by means of which two images of the surface, having a mutual phase difference and displacement, are superimposed on one another. The phase difference is provided between two beam components polarized orthogonally by means of an electro-optical modulator. Reasonably monochromatic radiation is converted by a collimator lens into a parallel beam of radiation applied to the electro-optical modulator. From the modulator, there emerge sub-beams, which are polarized at right angles to one another, and which differ in phase from one another. This effect is achieved by applying a suitable electrical potential in the direction of propagation of the radiation beam. The displacement of the components is effected in an interferometer which discriminates with respect to the direction of polarization. Using this method, a stable interferometer having no moving parts can be built.

Velzel describes a series arrangement of two Wollaston prisms, which produce opposite angle splittings between two orthogonally polarized sub-beams of light entering the series arrangement. The angular splitting occurring in the first Wollaston prism is compensated in the second such prism. However, since the compensation is not effected in the same plane as the splitting, the two beams are displaced from one another by a distance which may be continuously varied by varying the distance between the prisms.

The two Wollaston prisms shown by Velzel are similar in geometry, except that the crystal axes of the segments in the second prism of the series are rotated 90 degrees from the crystal axes of the corresponding segments in the first prism. This means that a beam consisting of orthogonally polarized sub-beams, entering the first prism parallel to the optical axis of the device is split to leave the second prism as two transversely displaced beams also parallel to the optical axis. Changing the lateral position of the Wollaston prism cannot be used to effect a change in the phase shift occurring between two beams reflected from the test specimen, since the symmetry of the compound prism prevents such a change from effecting the optical path lengths through the interferometer.

U.S. Pat. No. 4,320,973 to Fortunato et al shows the use of two Wollaston prisms of different sizes in series to receive a beam along the optical axis of the device, which is split into two diverging sub-beams in the first such prism to be brought back together at some distance past the second such prism. The intermediate plane of the second prism is inclined at an twice the angle and in the opposite direction when compared to the intermediate plane of the first prism.

In the *IBM Technical Disclosure Bulletin*, (Vol. 30, No. 11, p.p. 249-250), Makosch describes a method through which the diameter and spacing of the two laser light points produced by a device and reflected from a test surface are chosen independently of one another. A first lens focusses a collimated laser beam at the splitting plane of a first Wollaston prism, which splits the beam into two perpendicularly polarized partial beams diverging from one another at an angle. The two partial beams are redirected by means of a second lens in directions which would result in the beams being recombined in the intermediate image path of a microscope. However, before the two partial beams are recombined, they are deflected by a second Wollaston prism parallel to the optical axis of the device. In this manner, the laser light point is split in the intermediate image plane into two separate points. The spacing of these points changes linearly as a function of the spacing between the second Wollaston prism and the intermediate image plane at which recombination occurs. Thus, by moving the second prism along the optical axis, the spacing between the two points can be varied in a continuous (stepless) manner in this system from a value of zero to a finite value, without impairing the focussing of the points.

While a number of ways of building and using interferometers are described in these examples from the prior art, a method to use an interferometer in a way allowing the continuous scanning of a surface being examined is not found. Such a method is needed to match the capabilities of interferometry with the capabilities of processes for producing parts and devices which would benefit from examination by interferometry. In particular, a method for scanning the relatively large surfaces of silicon wafers used in the production of integrated circuits is needed. Also, a method is needed to provide for the automatic focussing of an interferometer to compensate for changes in the thickness of test samples. Furthermore, a method is needed to provide for the automatic control of the phase shift between reflected sub-beams, as required to maintain darkfield interferometry despite gradual variations in the angular orientation of a test surface.

SUMMARY OF THE INVENTION

In accordance with one aspect of the invention, there is provided a device for determining characteristics of a test surface of a test specimen. The device includes an instrument having an objective section for viewing the test surface, a mechanism for driving the test specimen so that the test surface is moved past the objective section in a preferred path, a defect detection mechanism, data storage, a location sensing mechanism, and first and second control mechanisms. The instrument also includes a first optical path directing an image of the test surface at the objective section to sensors sensing features of the image along a line, and a second optical path directing an image of the test surface to sensors sensing features of the image extending within an area. The sensors sensing features of the image along a line provide a first signal responsive to variations in the image. The defect detection mechanism detects variations in this first signal as the test specimen is driven to produce a flowing image on these sensors. he location sensing mechanism provides location data describing movement of the test surface past the objective section of the instrument. The first control mechanism stores this location data within data storage in response to the defect detection mechanism. The second control mechanism operates the mechanism for driving the test specimen into locations corresponding to the location data stored within data storage. The second control mechanism moves the test surface successively between these locations and holds the test surface at these locations as a stationary image of the test surface is projected on the sensors sensing features of the image extending within an area.

BRIEF DESCRIPTION OF THE DRAWINGS

A preferred embodiment of the subject invention is hereafter described with specific reference being made to the following Figures, in which:

FIG. 2 is a schematic cross-sectional plan view of a portion of an illumination arm of the interferometer of FIG. 1, taken as indicated by section lines II—II in FIG. 1;

FIG. 3 is a schematic cross-sectional elevation showing a light pattern projected from the illumination arm of the interferometer of FIG. 1, taken as indicated by section lines III—III in FIG. 1;

FIG. 5 is a schematic elevational view of a compound Wollaston prism built in accordance with an embodiment of the present invention;

DETAILED DESCRIPTION

Figure 1:
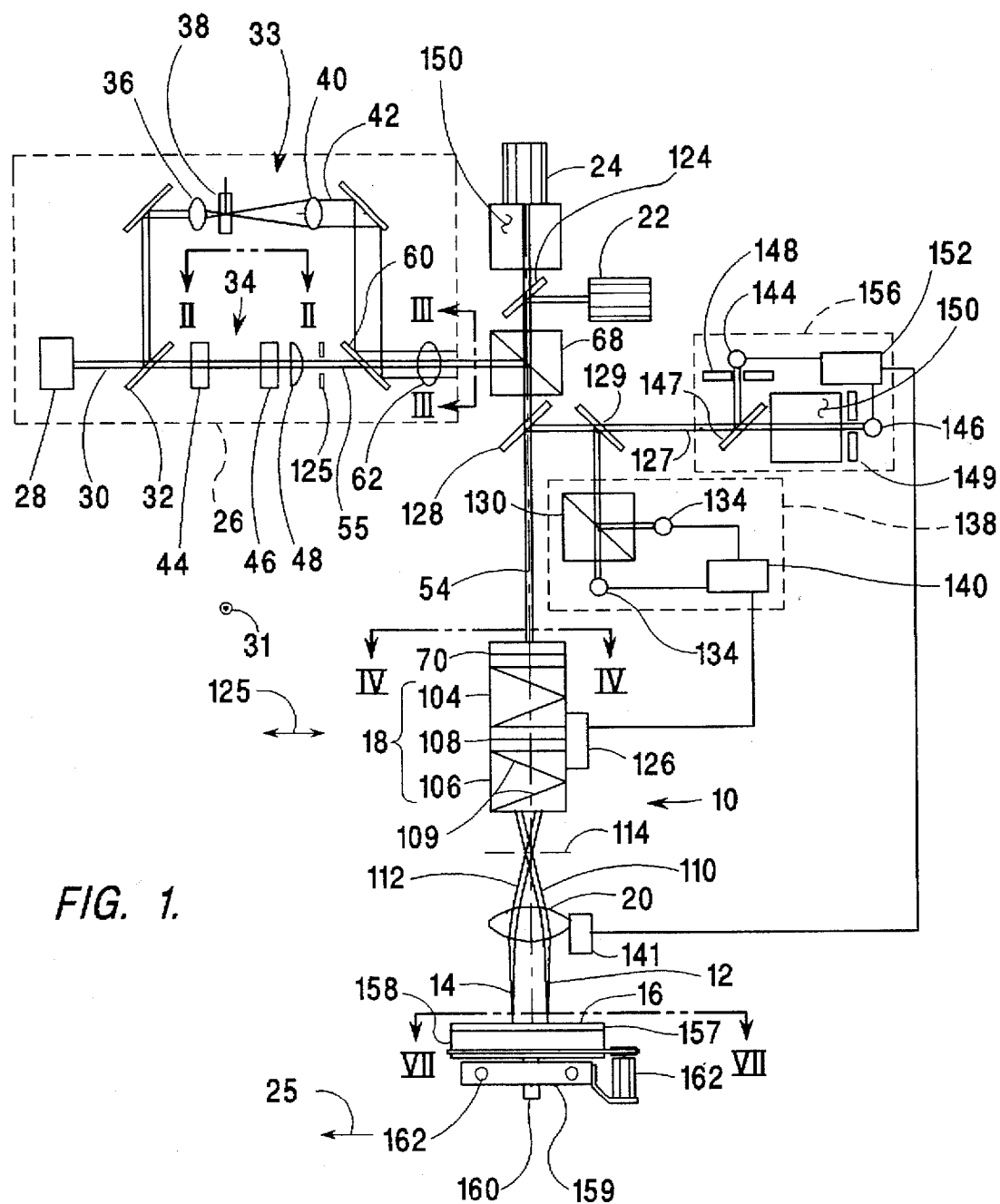
FIG. 1 is a schematic elevational view of an interferometer used within the present invention.

As shown in FIG. 1, an interferometer 10 is a common mode shearing type, producing a pair of sheared optical beams 12 and 14 both incident on a surface 16 being inspected. The sheared beams 12 and 14 are produced by a compound Wollaston prism 18, which projects a real splitting point in the rear focal plane of a microscope objective 20. The objective lens 20 forms interferograms of portions of surface 16 on both an area array CCD sensor 22, used for static surface acquisition, and a line scan CCD sensor 24, used for moving surface acquisition as the test surface 16 is moved past objective 20 in the direction of arrow 25. A dual-purpose illumination arm 26 provides both area and line illumination.

In the case of the acquisition of static surface information with area illumination, the interferogram at area array CCD sensor 22 is a dual image of the surface 16, with features laterally displaced by the amount of shear between beams 12 and 14 at test surface 16. These two images, formed using light beams of orthogonal polarities, are brought together at area array sensor 24. Since, when the two images are compared, the interference pattern resulting from an individual defect on test surface 16 is displaced, from one image to another, through the distance in which beams 12 and 14 are sheared, two interference patterns of such a defect appear, providing a form in which either interference pattern can be analyzed if the beams 12 and 14 are sheared sufficiently to avoid overlapping these patterns.

In the case of the acquisition of moving surface information, images of the two bright lines produced at the ends of sheared beams 12 and 14 along test surface 16, moving in the direction of arrow 25, are reflected upward through the interferometer 10, to be combined in an overlapping fashion at line scan CCD sensor 24. The illuminated lines formed on test surface 16 are sufficiently separated that a typical defect in test surface 16 appears in only one line at a time; therefore, only a single image of such a defect occurs at a time on the line of sensor 24.

Illumination arm 26 includes a laser 28, which produces a coherent and collimated light beam 30, having a diameter of about 0.7 mm, polarized to vibrate into and out of the plane of the drawing of FIG. 1, in the direction indicated by arrow 31. A beam splitting mirror 32 at the output of laser 28 divides the light beam 30 into a first portion directed along an upper light path 33 and a second portion directed along a lower light path 34.

Upper light path 33 includes a first lens 36, a diffuser 38, and a second lens 40 having a focal length substantially longer than that of first lens 36. Lenses 36 and 40 are arranged so that their focal points coincide at diffuser 38. In this way, while the light beam 42 projected from lens 40 is collimated, as is the light beam 30 from laser 28, light beam 42 has a substantially larger diameter than light beam 30. Diffuser 38 is included to improve the uniformity of light levels within light beam 42.

FIG. 2 is a schematic cross-sectional plan view of lower light path 34, taken as indicated by section lines II—II in FIG. 1. Various elements of this path are best understood by referring to both FIGS. 1 and 2. Thus, lower light path 34 includes a first cylindrical lens 44, a second cylindrical lens 46 and a third cylindrical lens 48, which are together arranged to produce an elongated light pattern of particular value in the inspection of a scanning, or moving test surface 16. Each cylindrical lens includes, for example, a flat surface 50 at one side and a curved surface 52, formed as a section of a cylinder, at an opposite side. First cylindrical lens 44 and second cylindrical lens 46 are both oriented so that the axes of their cylindrically curved surfaces 52 extend parallel to the optical axis 54 of interferometer 10. Third cylindrical lens 48 is oriented so that the axis of its cylindrically curved surface 52 extends perpendicularly to optical axis 54 and parallel to the direction indicated by arrow 31.

While the shape of the light beam 55 travelling along lower path 34, as viewed from the side, in the plane of FIG. 1, is virtually unchanged by first cylindrical lens 44 and second cylindrical lens 46, this beam is driven into a gradual convergence, or narrowing in this plane by passage through third cylindrical lens 48.

Referring to FIG. 2, first cylindrical lens 44 and second cylindrical lens 46 are arranged to have focal axes along a common line 56, extending parallel to the interferometer optical axis 54 (shown in FIG. 1). The radii of curvature of the curved surfaces of these lenses 44 and 46 are also chosen so that, as viewed in FIG. 2, light beam 54 is spread to a widened beam 55 passing through these cylindrical lenses. Because of its orientation, third cylindrical lens 48 does not significantly change the shape of light beam 55 as it is viewed in FIG. 2.

Referring again to FIG. 1, upper light beam 42 and lower light beam 55 are combined at a beam splitting mirror 60, to be projected into the remaining portion of interferometer 10 through a field lens 62.

FIG. 3 is a schematic view of the light beams projected from illumination arm 26, being taken as a cross-sectional elevation along section lines III—III in FIG. 1. Referring to FIG. 3, the light from upper path 33 is projected as a round collimated light beam 64, while the light from lower path 34 is projected as a horizontally oriented narrow beam 66. Both round beam 64 and narrow beam 66 are polarized in the direction of arrow 31, and both of these beams are collimated.

Referring again to FIG. 1, the light beams projected from illumination arm 26 are directed downward, along optical axis 54 by means of a polarizing beam splitter 68. Advantage is preferably taken of the fact that both light beams from illumination arm are polarized in the direction of arrow 31. It is possible to reflect up to 90 percent of the polarized light downward, along axis 54, while only 10 percent of this polarized light is transmitted through polarizing beam splitter 68. While only a relatively narrow beam is shown travelling through interferometer 10 outside illumination arm 26, this simplification has been provided simply to avoid obscuring the clarity of the drawing; it is understood that the relatively wide area beam from upper light path 33 is also present.

Figure 4:
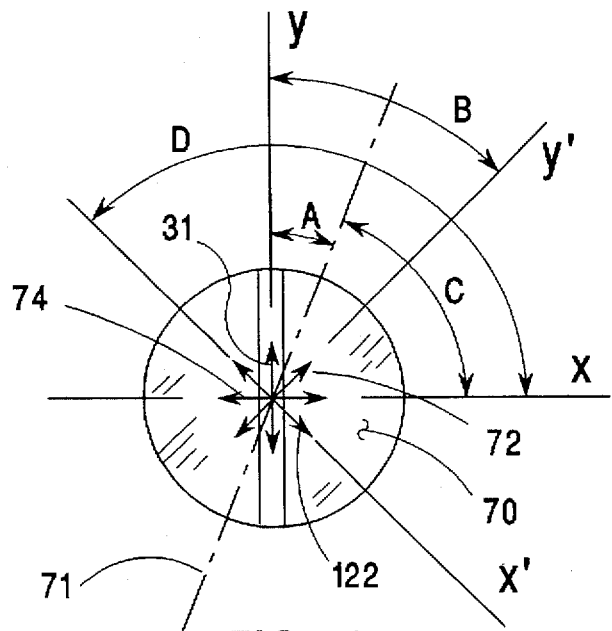
FIG. 4 is schematic cross-sectional plan view showing light patterns projected through a first half-wave plate of the interferometer of FIG. 1, taken as indicated by section lines IV—IV in FIG. 1.

FIG. 4 is a schematic plan view, taken as indicated by section lines IV—IV in FIG. 1, to show the transmission of light through a half-wave plate 70 placed atop compound Wollaston prism 18 (both shown in FIG. 1). Polarized light is transmitted downward to this plat 70 from polarizing beam splitter 68. A coordinate system has been applied within this figure to simplify the discussion of certain concepts. Thus in FIG. 4, the direction extending to the right of FIG. 1, is defined as the x-direction, while the direction into the paper of FIG. 1 is defined as the y-direction.

Referring to FIG. 4, the transmission of linearly polarized light through a half-wave plate, such as plate 70, results in rotation of the angle of polarization through an angle which is twice the angle between the crystal axis of the material composing the half-wave plate and the axis of polarization of light entering the plate. The light reflected from polarizing beam splitter 68 enters half-wave plate 70 polarized along a y-axis, in the direction of arrow 31. The crystal axis of half-wave plate 70 is parallel to line 71, at a 22.5-degree angle, indicated as angle A, from this plane of polarization. Therefore, light leaves plate 70 polarized in the direction of arrow 72, with the plane of polarization having been rotated through a 45-degree angle, indicated as angle B.

While light subsequently enters prism 18 polarized in the direction of arrow 72, at a 45-degree angle with respect to the crystal axes of the each segment of prism 18, the interaction between this polarized light and the crystal structure within Wollaston prism 18 results in the polarized light transmitted downward through the prism 18 being effectively broken into equal portions of light polarized in the directions of arrows 31 and 74. The light entering prism 18 is the vector sum of the light transmitted through the prism polarized in the direction of arrow 31 and the light transmitted through the prism polarized in the direction of arrow 74.

FIG. 5 is a schematic elevational view of a compound Wollaston prism configured and used in the manner of the present invention. In order to simplify discussion of the paths of individual light rays, the design of the various elements has been simplified, with each individual Wollaston prism being shown as a two-element device, instead of the three-element device shown in FIG. 1. However, the operation of the apparatus of FIG. 5 is similar to that of the apparatus of FIG. 1, and either type of apparatus may be used in the practice of the present invention.

Referring to FIG. 5, a compound Wollaston prism 76 includes a first two-element Wollaston prism 78 and a second two-element Wollaston prism 80. A half-wave plate 82 is placed between the prisms 78 and 80. All of the elements of prisms 78 and 80 are made of a birefringent material, such as quartz. The half-wave plate 82 may also be made of quartz. The two elements 83 and 84 of first prism 78 are adjacent along an intermediate plane 85 at an oblique angle to the optical axis 86 of the device. Both outer surfaces 87 and 88 of prism 78 are perpendicular to optical axis 86. Elements 83 and 84 have crystal axes which are perpendicular to each other and to optical axis 86. One of these crystal axes is parallel to intermediate plane 85.

Second Wollaston prism 80 is similar in composition to first prism 78, with the first element 89 and second element 90 crystal axes parallel to the crystal axes of first element 83 and second element 84 of first prism 78, respectively. However, intermediate plane 91 of second prism 80 is not parallel to intermediate plane 85 of first prism 78, and the thicknesses of corresponding elements, in the direction of optical axis 86, may vary between the two prisms.

An incoming light ray 92 is directed parallel to optical axis 86 of the device, being polarized at a 45-degree angle to both crystal axes of the elements in prism 78. As explained above in reference to FIG. 4, within prism 78, this ray 92 is divided into a first ray 94 and a second ray 96, which are polarized orthoganally to one another. These rays 94 and 96 begin diverging at intermediate plane 85 due to the birefringent property of the material of which prism 78 is composed.

Figure 6:
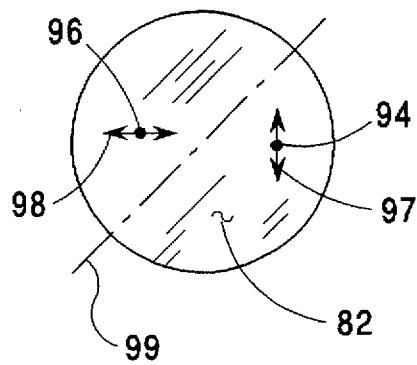
FIG. 6 is a schematic cross-sectional plan view showing light patterns projected through a half-wave plate within the compound Wollaston prism of FIG. 5, taken as indicated by section lines VI—VI in FIG. 5.

Referring to FIG. 6, a cross-sectional diagram taken as indicated by section lines VI—VI in FIG. 5, light ray 94 enters half-wave plate 82 polarized in a direction indicated by arrow 97, while light ray 96 enters plate 82 polarized in a direction indicated by arrow 98. The crystal axis of the material of half-wave plate 82 is parallel to line 99, lying at a 45-degree angle with respect to the planes of polarization of both light rays 94 and 96. Thus, the planes of polarization of both light rays 94 and 96 are rotated 90 degrees as these rays pass through the plate 82.

Referring again to FIG. 5, this rotation of the planes of polarization causes light ray 94, which was refracted toward the right (as viewed in the figure) as it is transmitted through first prism 78, to be refracted back toward the left as it is transmitted through second prism 80. Similarly, light ray 96, which was refracted toward the left during transmission through first prism 78 is refracted toward the right during transmission through second prism 80. Thus, the resulting light rays 100 and 101 leaving second prism 80 converge at an intersection point 102.

A microscope objective lens 103 is preferably located so that its focal point lies at the intersection point 102 of light rays 100 and 101. Since these rays 100 and 101 pass through the focal point of the lens 103, they are refracted to travel parallel to each other and to the optical axis 86 upon leaving the lens 103.

Referring again to FIG. 1, compound Wollaston prism 18 is made up of a first Wollaston prism 104 and a second Wollaston prism 106, together with an intermediate half-wave plate 108 having a crystal axis placed at an angle of 45 degrees relative to the directions of polarization of light travelling between first prism 104 and second prism 106, as described above in reference of FIG. 6. Despite the additional elements in compound prism 18, this compound prism 18 functions in a manner similar to that described above in reference to FIG. 5. Compound Wollaston prism 18 is like compound Wollaston prism 75 (of FIG. 5) in that the first and second prisms 104 and 106 differ, for example, in the angles of their intermediate planes 109 and the thicknesses of their components in the direction of optical axis 52.

However, since the light beams provided by illumination arm 26 are collimated beams, cross-sectionally shaped as shown in FIG. 4, instead of the individual rays discussed in reference to FIG. 5, these beams leave compound Wollaston prism 18 as collimated beams 110 and 112, which are individually directed inward while remaining polarized orthogonally to each other.

A microscope objective lens 20 is preferably placed with a rear focal plane 114 aligned at the intersection of central rays within the beams 110 and 112, and with a front focal plane aligned at test surface 16. In this way, each beam 110 and 112 is refracted to leave lens 20 in a direction parallel to optical axis 54, and the two beams are individually condensed, with the lines formed by light from lower path 34 in illumination arm 26 forming two small, bright lines of light. In this way, a real split splitting point is projected to the rear focal plane of the objective lens 20, even if this plane is physically inaccessible.

Thus, while the orthoganally polarized rays of the interferometer described in U.S. Pat. No. 3,849,003 to Velzel leave the second Wollaston prism in a direction parallel to the optical axis of the device, the rays of interferometer 10 leave the second Wollaston prism 106, being directed toward the optical axis of the device. This arrangement of interferometer 10 provides for flexibility in the projection of a real splitting point while avoiding a need for an objective lens to drive the various rays back into convergence. Furthermore, the placement of a lens between the two Wollaston prisms, as advocated by Makosch in the *IBM Technical Disclosure Bulletin*, Vol. 10, No. 11, p.p. 259–250, is not required to bring the rays back into convergence.

Figure 7:
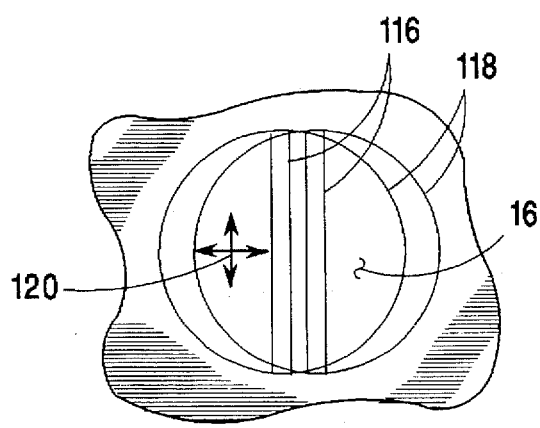
FIG. 7 is a schematic plan view of a light pattern produced by the interferometer of FIG. 1 on a surface being tested, taken as indicated by section lines VII—VII in FIG. 1.

FIG. 7 is a cross-sectional plan view, taken as indicated by section lines VII—VII in FIG. 1, schematically showing the illumination pattern thus produced on surface 16. This illumination pattern includes a pair of brightly illuminated lines 116, resulting from the light transmitted along lower path 34 of the illumination arm 26, and a pair of illuminated areas 118, resulting from the light transmitted along upper path 33 of the illumination arm. The light in this illumination pattern is orthogonally polarized in the planes indicated by crossed arrows 120, with one of the illuminated lines 116 and a corresponding illuminated area 118 being polarized in one such plane, while the other illuminated line 116 and the other illuminated area 118 are polarized in the other such plane. The illumination pattern provided by illuminated lines 116 is particularly useful for measuring a test surface 16 moving in a scanning motion in the direction indicated by arrow 25 (or in the direction opposite to arrow 25), while the illumination pattern provided by areas 118 is particularly useful for measuring a test surface 16 held in a stationary condition.

The light from the lower path 34 may be focused, for example, into a pair of lines, each of which has a width of 4 microns, separated by a center-to-center distance of 60 microns. This center-to-center distance is the shear distance of the interferometer, effecting the displacement of the circular illuminated areas 118 as well.

Residual straight fringes in the interferometer 10 may be removed by the choice of splitting angles, with splitting angles preferably being chosen to create a splitting plane perpendicular to the optical axis 54. Residual hyperbolic fringes are removed by having the second Wollaston prism 106 compensate for the first Wollaston prism 104.

The illumination from orthogonally polarized beams 12 and 14 is reflected from test surface 16 to be returned through microscope objective 20 and compound Wollaston prism 18 along the paths traveled by light moving downward toward test surface 16 from polarizing beam splitter 68. At half-wave plate 108, the directions of polarization of both reflected light beams are rotated 90 degrees, as previously described in reference to half-wave plate 82 (shown in FIG. 6). This rotation prepares the light beams to be recombined by first Wollaston prism 104.

Referring again to FIG. 4, light reflected from test surface 16 (shown in FIG. 1) enters the lower surface of half-wave plate 70 with one beam polarized in the direction of the x-axis, as indicated by arrow 74, while the other beam is polarized in the direction of the direction of the y-axis, as indicated by arrow 31. Since the crystal axis of plate 70 is parallel to line 71, at a 22.5-degree angle A with respect to the y-axis, the polarization angle of light polarized in the direction of arrow 31 is rotated through a 45-degree angle B, to a direction of polarization indicated by arrow 72. Since the crystal axis of plate 70 is at a 67.5-degree angle C relative to the x-axis, the polarization angle of light polarized in the direction of arrow 74 is rotated through a 135-degree angle D, to a direction of polarization indicated by arrow 122. For continued reference, the axis of polarization of the light which was previously polarized along the y-axis is defined as the y'-axis, and the axis of polarization of the light which was previously polarized along the x-axis is defined as the x'-axis.

Referring again to FIG. 1, a portion of this reflected light continues along optical axis 54, past polarizing beam splitter 68, to a beam splitting mirror 124, which directs a portion of the light to the area CCD array of sensor 22 and a remaining portion of the light to the line scan CCD array of sensor 24. During the use of the interferometer 10 to acquire information about a moving surface, with a line of illumination projected on sensor 24, both line illumination through lower illumination path 34 of illumination arm 26 and area illumination through upper illumination path 33 are provided. In this application of interferometer 10, it is not necessary to block the upper illumination path 33, since the intensity of illumination provided through this path is much lower than the intensity of the illuminated lines 116 (shown in FIG. 7). On the other hand, when interferometer 10 is used to acquire information about a static surface through area illumination provided by upper illumination path 33, the light from lower illumination path 34 is blocked by closing a shutter 126 in this path.

A method for controlling the phase angle between the two orthogonally polarized light beams returned upward to sensors 22 and 24 will now be discussed, at first with continuing reference being made to FIG. 1.

Compound Wollaston prism 18 is mounted within the interferometer 10 in a manner allowing lateral motion along a line extending perpendicular to the optical axis of the compound prism 18, in either direction indicated by arrow 125. The compound prism 18 is moved laterally by means of a piezoelectric actuator 126. Since the first prism 104 and the second prism 106 are different in such parameters as the angles of intermediate planes 109 and the thicknesses of segments, this lateral movement of compound prism 18 changes the relative path lengths traveled by the two light beams 110 and 112. Since a change in relative path lengths introduces a phase angle difference between the two light beams 110 and 112, the lateral movement of compound prism 18 is used to control the phase angle between the sheared optical beams 12 and 14. The phase difference generated in this way can be used to bias the operation point of the interferometer 10. This phase difference may alternately be used in compensating for the tilt of surface 16, as such tilt introduces a phase shift between the sheared beams 12 and 14.

Interferometer 10 is usually operated to produce a darkfield interferogram, having a dark background caused by cancelling, through the interference phenomenon, of light reflected from the flat surface of test sample 16. Both bumps and depressions in the surface result in the appearance of illuminated interference patterns on the dark background. This type of pattern usually proves to be the easiest pattern to read. This darkfield effect occurs when the two orthogonally-polarized light images reflected from the flat portion of test surface 16 are 180 degrees out of phase.

Referring again to FIG. 4, as previously discussed, light reflected from test surface 16 leaves half-wave plate 70 as two beams orthogonally polarized along the directions of the x'- and y'-axes. While it is understood that this light pattern can alternatively be considered as beams polarized along other orthogonal axes, examining the light in terms of polarization along the x'- and y'-axes is particularly useful, since the components of light polarized along these axes correspond to the orthogonal components of light reflected at the test surface, polarized along the x- and y-axes. If the beams polarized along the x'- and y'-axes are 180 degrees out of phase, as the light level of a beam polarized along the x'-axis increases from the origin in the x' direction, the light level of the beam polarized along the y'-axis increases similarly from the origin in the -y' direction. These two beams are resolved into a single beam increasing at this point in the -y direction. Thus, the two beams polarized along the x' and y' axes, 180 degrees out of phase, are resolved as a single beam polarized along the y axis. At the other extreme, when the two beams polarized along the x'- and y'-axes are in phase, as the light level of the beam polarized along the x'-axis increases from the origin in the x' direction, the light level of the beam polarized along the y'-axis increases from the origin in the y' direction. These two beams are resolved into a single beam increasing at this point in the x direction. Thus, the two beams in phase are resolved as a single beam polarized along the x axis. Other phase relationships between light beams 122 and 124 do not resolve into a single linearly polarized beam.

Referring again to FIG. 1, the 180-degree out of phase condition required for darkfield interferometry can thus be readily detected by measuring the light levels returned along optical axis 54 above half-wave plate 70, polarized in orthogonal directions. Toward this purpose, a fraction of the light reflected from surface 16 is directed along a split optical path 127 by a beam splitting mirror 128. A portion of the light directed along optical path 127 is directed by another beam splitting mirror 129, to a polarizing beam splitter 130, providing for the transmission of light at a first polarization to a photodetector 134 and for the reflection of light polarized orthogonally to the first polarization to the other photodetector 134. The angle of the first polarization may be changed by varying the construction of polarizing beam splitter 134. For example, the crystal angle of the materials composing beam splitter 134 may be varied for this purpose. Polarizing beam splitter 134 is preferably configured so that a portion of the light traveling upward from half-wave plate 70, polarized in the direction of the x'-axis is directed into one of the photodetectors 134, while a portion of this light polarized in the direction of the y'-axis is directed into the other of the photodetectors. Photodetectors 134 form part of a optical phase servo system 138, which drives piezoelectric actuator 126 to move compound Wollaston prism 18 laterally.

Changes in the state of polarization of the light received along split optical light path 127, occurring due to tilt of surface 16, result in a differential error signal, which is fed back to a controller 140 within servo system 138 to close the control loop. The relative phase control servo system 138 can be set to move the compound prism 18 so that any state of optical phase bias is produced in the interferometer 10, from a darkfield at a phase difference of 180 degrees to a brightfield at a phase difference of 0 degrees, and to make whatever corrections are necessary to maintain the apparatus in any such state.

If polarizing beam splitter 130 is configured according to the preferable method described above, under both brightfield and darkfield conditions the output of the two photodetectors 134 is equal. The overall output of one of the sensing arrays 22 or 24 may be applied as an input to controller 140 to allow discrimination between brightfield and darkfield conditions.

Alternatively, polarizing beam splitter 130 may be configured so that a portion of the light travelling upward from half-wave plate 70, polarized in the direction of the x-axis is directed into one of the photodetectors 134, while a portion of this light polarized in the direction of the y-axis is directed into the other of the photodetectors 134. With this alternative, to obtain and maintain darkfield operation, compound Wollaston prism 18 may be moved so that the output of the detector 134 measuring light polarized in the direction indicated by arrow 125 is driven to zero, while the output of the detector 134 measuring light polarized in the direction indicated by arrow 31 is maximized.

An autofocus system is used to maintain the focus of the main imaging path of interferometer 10. The objective lens 20 is mounted in a way allowing motion in either direction along device optical axis 54. This lens 20 is moved by a piezoelectric actuator 141 in response to changes in the average position of surface 16, which may be caused, for example, by variations in the thickness of the part being examined. These changes in surface position are detected using a pair of photodetectors 144 and 146. A beam splitting mirror 147 is provided within split optical path 127, so that a portion of the light transmitted past beam splitting mirror 129 is reflected to photodetector 144, while the remainder of this light is transmitted to photodetector 146. Slit aperture plates 148 and 149 are placed between the split optical path 127 and photodetectors 144 and 146.

The CCD arrays of area sensor 22 and line sensor 24 are arranged to have equal optical path lengths to half-wave plate 70. A glass spacer 150 may be included in one of these paths to aid in the achievement of equal optical path lengths. When objective lens 20 is properly focussed on test surface 16, a maximum level of illumination is reached at the central part of the image formed at the CCD array of either sensor 22 or 24. At optical path distances greater than or less than the distance to these CCD arrays, the illumination returning from reflection off test surface 16 is spread out. Thus, the illumination pattern is said to have a "waist," with the narrowest portion at each of the CCD arrays.

The slits in aperture plates 148 and 149 are arranged so that photodetectors 144 and 146 view only a narrow central portion of the reflected light beam. While the optical path length from half-wave plate 70 to aperture plate 148 is somewhat shorter than the optical path length from plate 70 to one of the CCD arrays 22 or 24, the optical path from plate 70 to aperture plate 149 is somewhat longer than the optical path length to one of the CCD arrays 22 or 24. A glass spacer 150 may be used to help establish the appropriate optical path lengths. When objective lens 20 is properly focused on target surface 16, equal illumination levels are read by photodetectors 144 and 146, so lens 20 is held in position. When photodetector 144 receives more light than photodetector 146, indicating that the waist of the illumination profile is closer to aperture 148 than to aperture 149, lens 20 is moved in a direction which moves the waist outward along the optical path. Similarly, when photodetector 146 receives more light than photodetector 144, indicating that the waist of the illumination profile is close to aperture 149 than to aperture 148, lens 20 is moved in a direction which moves the waist inward along the optical path. To provide these movements, the outputs of photodetectors 144 and 146 are directed to an autofocus controller 152 within autofocus servo system 156. A difference between the outputs of photodetectors 144 and 146 results in the generation of a differential error signal within controller 152, which in turn results in the variation of the control signal provided from controller 152 to piezoelectric actuator 141.

While many types of objects with high reflectivity can be inspected using interferometer 10, an important application of the device in examining the surface of a disk-shaped test object 157, such as the disk manufactured for use as a storage medium. To further facilitate the acquisition of such surface information, a chuck 158, rotatably mounted in a carriage 159 and driven about a pivot shaft 160 by a motor 162, is provided to hold the test object 157 and to drive its surface 16 past the illuminated lines 12 and 14 in the direction of arrow 25. A vacuum clamp or other hold down means may be provided to hold test object 157 in place on chuck 158. Carriage 159 is in turn driven in either of the directions indicated by arrow 31 by means of a leadscrew 162. The resulting motion causes the interferometer 10 to view a spiral portion of surface 16 of disk 156.

The scanning capabilities of interferometer 10, whether used to scan a disk surface in a spiral fashion as described or to scan a surface driven past the interferometer in a linear fashion are critically important in an effort to develop a method for inspecting various types of parts. As described above, the scanning process can be performed in an automated manner, without stopping to repeat setting up the device, while the relative phase control servo system 138 operates to compensate for gradual changes in the angular alignment of the test surface being viewed, and while the autofocus servo system 156 operates to compensate for gradual changes in the elevation of the test surface being viewed.

Figure 8:
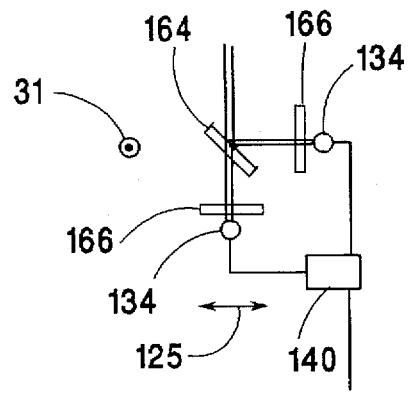
FIG. 8 is a schematic elevational view of an alternative beam splitting portion of a phase angle control servomechanism built in accordance with the present invention.

FIG. 8 shows an alternative construction of a mechanism for providing feedback concerning the phase angle between the orthogonally polarized beams returned as reflections from test surface 16. Instead of the polarizing beam splitter described above in reference to FIG. 1, a beam splitting mirror is provided to divide light between the two photodetectors 134. A polarizing plate 166 is provided between each photodetector 134 and the mirror 156. These plates 166 are arranged so that light polarized in one direction passes through to one of the photodetectors 134, while light polarized orthogonally to this direction passes through to the other of the photodetectors 134. The output of the photodetectors 134 are used as described above to control phase shift.

Referring again to FIG. 1, in a typical application of the surface profile interferometer 10, the disk media of a hardfile is measured to determine smoothness to a few nanometers. In accordance with the present invention, an automated procedure is provided for first scanning the disk using the line scan CCD sensor 24, determining where defects are detected in the disk surface. The location of each such defect is stored, and, after the line scan process is completed, each defect is detected using the static area scan technique available through the use of area sensor 22.

The basic technique of measurement uses laser darkfield shear length interferometry, yielding darkness corresponding to the smooth areas while defects appear as spots of brightness. In this measuring process, the disk 157 is scanned in a spiral motion, rotating with spindle 160 as this spindle 160 is also driven in a linear motion by carriage 159. The surface 16 of the disk 157 is illuminated with the interferometer. The line scan CCD sensor 24 follows this scan, recording bumps or pits in the disk surface as bright spots. Fortunately, the vast majority of a typical disk is recorded as blackness, indicating that the disk is flat within desired limits. For example, a 95-mm disk produces approximately 460 Mbytes of data, almost all of which are typically null data without value.

Figure 9:
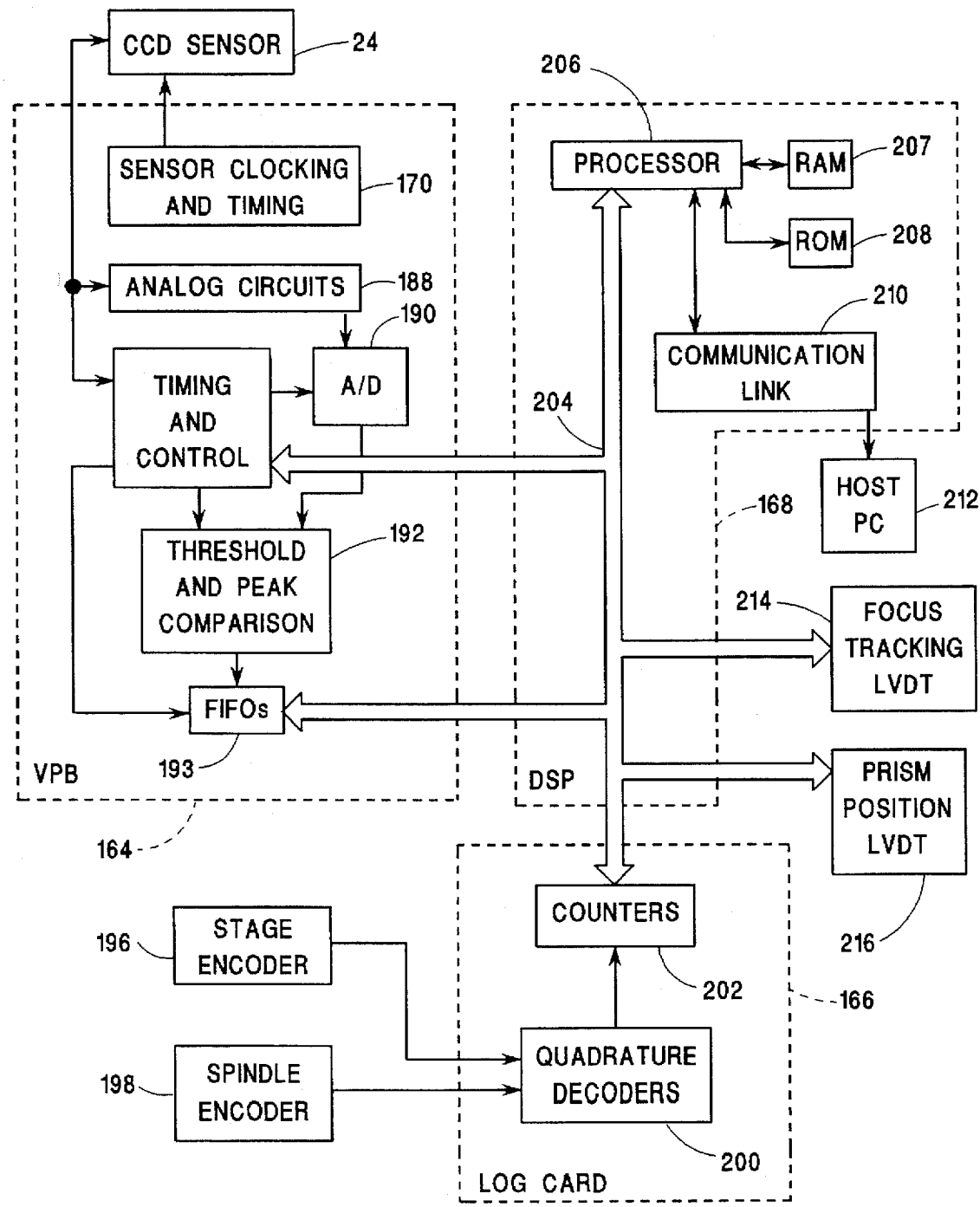
FIG. 9 is a block diagram of a video preprocessing system for acquiring data from a line scan CCD sensor within the interferometer of FIG. 1.

FIG. 9 is a block diagram of a video preprocessing system, which sorts through this data, arriving at a rate of 20 million samples per second from the output of CCD line scan sensor 24. This system discards the null data, storing the valuable data with tags that locate each datum to a point on the disk surface. The video preprocessing system consists of three main parts—a video processor board (VPB) 164, which powers and clocks line scan sensor 24 while processing and returning data from the sensor 24; a position logging card (log card) 166, which reads the outputs indicating the rotational position of spindle 160 and the linear position of carriage 159; and a digital signal processor (DSP) 168, which processes data from the VPB 164 and the log card 166 to produce a location map of detected features.

Figure 10:
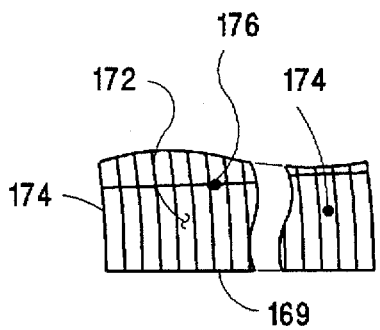
FIG. 10 is a schematic elevational view of a line scan CCD sensor within the interferometer of FIG. 1, which further indicates a portion of the surface examined during a single video line scan of a test sample by this sensor.

FIG. 10 is a schematic elevational view of line scan CCD sensor 24 within the interferometer of FIG. 1, with additional indications of a portion of the surface examined during a single video line scan of a test sample by this sensor. The sensor 24 includes 1063 pixel elements 169, of which 1024 are active pixel elements, each of which measures the illumination level of an interferogram corresponding to an area which is 0.6 microns wide. Thus, the interferogram of a portion of the test surface 16, having a width of 614 microns, is viewed by the line scan CCD sensor 24.

Referring to FIGS. 9 and 10, the VPB 164 functions as a controller for the CCD sensor 24, powering and clocking the sensor 24 as well as processing returning video data. In sensor clocking and timing circuits 170, the VPB 164 generates a 20 MHz (megahertz) clock with a line synch pulse every 1063 clock cycles. This synch pulse causes the CCD elements within the sensor 24 to be dumped to their associated shift register and to begin transferring data to the VPB 164. During the scanning process, a scan of a video line, providing data from each of the 1063 pixels, occurs with each clock pulse from the sensor clocking and timing circuits 170. Since these pulses occur at a rate of 20 MHz, the time between pulses is 50 nanoseconds, and the line synch pulse between line scans occurs every 53.15 milliseconds.

As previously described in reference to FIGS. 1 and 7, the interferometer 10 produces two polarized, illuminated lines 116 on the surface 16 being examined. Therefore, each measurable defect in this surface 16 results in two images, or brightspots in the darkfield, being sequentially detected through the line scan CCD sensor 24. These two lines are separated by 60 microns, the shear distance of the interferometer 10.

Since the timing between video line scans is held at 53.15 milliseconds, the distance travelled by the surface 16 being examined between video lines is determined by the speed at which the surface is driven. Preferably, this distance travelled is set at a submultiple of the shear distance, so that the two images arising from a single defect are more easily identified and related to one another. In the present application of examining hardfile media, the distance is preferably set to 30 microns, or half the shear distance. Different types of surfaces are most effectively examined with this distance set at different submultiples of the shear distance. With 53.15 milliseconds between video scans, the desired distance of 30 microns is obtained by setting the velocity at 0.5644 meter/second. Under these conditions, the line scan in which the second image of a defect is detected is usually the second line scan behind the line scan in which the first image of the defect is detected. In the present application, this velocity is held at a constant level while examining a spiral pattern on a disk-shaped surface by decreasing the angular velocity of the spindle 160 as carriage 159 (both shown in FIG. 1) moves the area being examined away from the center of the disk.

Referring again to FIG. 10, this scanning process divides the surface being examined into 1024 pixels 172, each of which represents the surface conditions of a spiral arc 0.6 microns wide and 30 microns long. The entire video scan represents the surface conditions of a spiral arc 174, which is 614 microns wide and 60 microns long. In the CCD array of sensor 24, there are 1063 pixel elements, 1024 of which are active, containing valid data. The remaining pixel elements provide control and video information that is not valid data. The VPB 164 (shown in FIG. 9) ignores these non-informative pixels and examines the active pixels.

Since only one output is provided from each pixel element during each video line scan, an area integration is produced within each pixel 172. That is, the brightness levels associated with two or more defects 174 in the same pixel are added to produce the output of that pixel. Nevertheless, this method of scanning produces valuable results, particularly since a single measurable defect, or multiple defects, within a particular pixel is a relatively rare event. A further form of integration is provided by the process when, for each line scan having one or more detected defects, the intensity of the pixel having the greatest intensity is stored as a single maximum intensity level associated with the line scan.

On the other hand, a single defect 176 may occur at a boundary between pixels within sequentially adjacent video line scans. This occurrence does not present a problem, except that, due to the effect of area integration within each pixel 172, the resulting output for each of the pixels may be below the threshold level, so that a defect which should be detected is missed. To avoid this occurrence, the process of the present invention examines the maximum intensity levels of adjacent integrals, determining if their combination should result in the detection of a defect.

Figure 11:
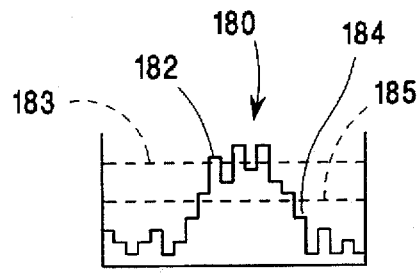
FIG. 11 is a graphical view of the output of a line scan CCD sensor of FIG. 10.

FIG. 11 is a diagram of the output signal from the line scan LCD sensor 22, in which the individual levels 178 indicate the intensity output levels of individual pixel elements 169 (shown in FIG. 10), as the intensities of these pixel elements are sequentially clocked out at the clock rate of 50 MHz. A measurable level of noise associated with this signal causes relatively small differences in the intensities of adjacent pixel elements. A generally bell-shaped curve 180 indicates that a defect is being detected. This shape is determined both by the size of the defect and by the fact the optical system of interferometer 10 cannot be perfectly focussed. The detection of a defect is begun with the first pixel element output 182 above a beginning threshold level 183. The detection of a defect is then ended with the first pixel element output 184 below an ending threshold level 185. Thus a differential zone of output voltages, in which the detection of a defect may be begun but not ended, is provided between the two threshold levels 183 and 185. If the beginning and ending threshold levels were instead at the same level, the presence of a single defect having an intensity near the threshold level would cause the false detection of several defects, as the noise on the signal would turn the detection process on and off. This gap between the threshold levels 183 and 185 may be implemented by storing the two threshold levels. Alternately, a single threshold level, corresponding to the ending threshold level 185 may be used for both comparisons, if certain low-order bits from the digital code representing the beginning intensity signal are ignored, forcing this signal to be actually higher to start the detection of a defect.

Referring again to FIG. 9, as well as to FIG. 11, data coming into VPB 164 passes through analog circuitry 188, to be digitized in an A/D convertor 190, before being delivered to a video processing section 192, where the data is compared to the threshold levels 183 and 185. If all the data from an individual video scan is below the beginning threshold level 183, the intensity data is discarded, and a single, end of integral, code is sent at the end of the scan for synchronization, along with an indication of the maximum pixel intensity of the video scan line.

Figure 12:
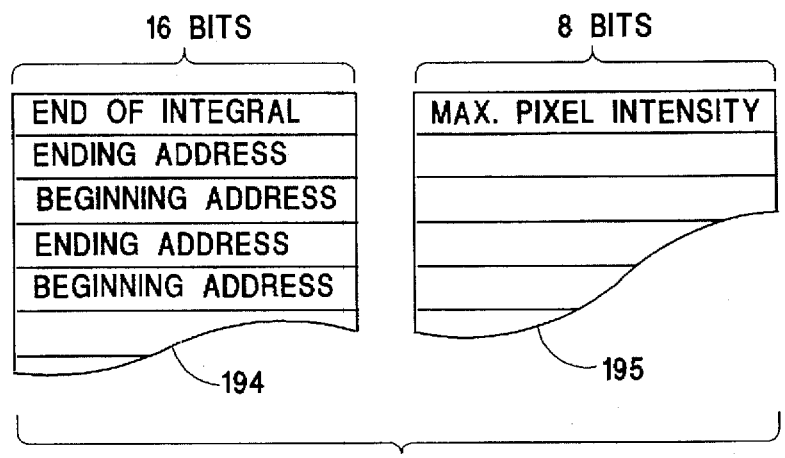
FIG. 12 is a schematic diagram of FIFO buffers within the preprocessing system of FIG. 9.

FIG. 12 is a schematic diagram of the FIFO registers shown as 193 in FIG. 9. These registers are composed of a 16-bit address register 194 and an 8-bit data register 195.

Referring to FIGS. 9–12, if the intensity level from a pixel element 169 beginning the detection of a defect exceeds the beginning threshold level 183, the video processing section 192 stores the pixel number of that pixel element 169 in address memory 194. For each pixel, regardless of whether the VPB state is above or below threshold level, the current maximum pixel intensity is compared to the current pixel intensity. If the current pixel intensity is greater, a new maximum pixel intensity is stored. If a data value falls below the ending threshold level 185, the pixel number of the pixel element 169 providing the data value is stored as the ending address in address register 194. If another defect is detected, this process is repeated. With the synch pulse from sensor clocking and timing circuits 170, an all-zeros end of integral marker is recorded in the address register, and the maximum pixel intensity stored internally by the video processing section 192 is stored in the data register 195. Thus, for each transition of the intensity signal above the beginning threshold level, starting and ending pixel addresses are stored in address buffer 194. For each video scan, or integral, having such a transition, a maximum pixel intensity is stored in the data register 195. The starting and ending addresses provide the width of each feature and the distance offset from the edge of the video scan. The peak video value, along with this width, provide information concerning the overall size of the feature.

Referring again to FIG. 9, the log card 166 is used, in conjunction with the pixel addresses from VPB 164, to determine the position of a feature on the disk. The log card records the position of carriage 157 and spindle 150 as the disk 157 is driven to inspect a spiral pattern on the test surface 16 (all shown in FIG. 1). This data is obtained from optical position encoders 196 and 198, providing the position of the carriage and spindle, respectively. Within log card 166, quadrature decoders 200 decode the signals from encoders 196 and 198 to make a relatively course determination of the location of the carriage 157 and spindle 150, while counters 202 count pulses from the encoders to make a fine determination of these locations. Each time VPB 164 sends a synch signal indicating that a new video line has just begun, the log card 166 is triggered to latch the radial (carriage) and rotational (spindle) positions. When the pixel address is added to the radial position, the resulting data provides the location of the feature on the disk, in the form of a radius and an angle theta. In this way, a position metric is produced to be stored with the feature data. This function is critical to the video preprocessing system, since the position of data is otherwise lost as the null data is discarded.

Both VPB 164 and log card 166 attach to DSP 168, by means of DSP bus interface 204. DSP 168 includes a processor 206, random-access memory (RAM) 208, read-only memory (ROM) 210, clocks and system timing, analog to digital converters, and a communication link 210 to a host personal computer (PC) 212. The DSP 168 synchronizes and controls operations of the VPB 164 and log card 166, producing data for each detected feature, consisting of the position, magnitude, and width of the feature. The DSP 168 also combines information about features that span sequentially adjacent video scan lines, producing composite feature data.

Referring again to FIG. 1, as previously discussed, the objective lens 20 is moved along optical axis 54 by means of a piezoelectric actuator 141, as part of an autofocus system responding to variations in the thickness of the part being examined, such as the disk 157. Also, Wollaston prism 18 is moved in the direction of arrow 125 by an automatic system driving an actuator 126 to maintain the phase angle difference between the two polarized light beams striking the surface being examined. In the type of system operation now being described, this phase angle difference is controlled to maintain a darkfield.

Referring again to FIG. 9, a Linear Variable Displacement Transducer (LVDT) 214 tracks the position of objective lens 20 as it is varied with piezoelectric actuator 141, and a prism position LVDT 216 tracks the position of the Wollaston prism 18 as it is varied by the operation of actuator 126. Since these movements are made in response to changes in the location or angle of the surface being examined, they provide an indication of the general flatness or runout of the disk. Therefore data from these sensors 214 and 216 is also collected by the DSP 168.

The DSP 168 packs all of this data, forwarding it to the system host computer 212, where maps of features and of parameters, such as disk runout, are produced. On a typical high-quality disk blank having fewer than ten detectable features, the quantity of data sent to the host computer is a very small fraction of the data sent from CCD sensor 24 and sensors 214 and 216. With this system, instead of the 450 Mbytes which could be required without such techniques, a few hundred bytes are used to mark and identify all features of interest.

Figure 13:
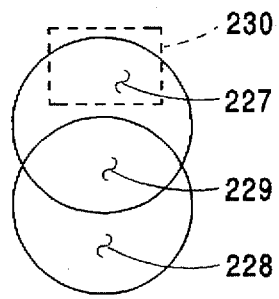
FIG. 13 is a schematic elevational view of areas of significance in an interferogram produced at an area array CCD sensor in the interferometer of FIG. 1.

FIG. 13 is a schematic diagram showing areas of interest in an interferogram which may be produced using static scan area CCD sensor 22. A first area 227 includes positive image information describing the defect. A second area 228 includes negative image information describing the defect. Since an overlapping area 229 includes both positive and negative images of the same defect, it cannot be used to provide valid data describing the defect. The dashed lines represent a bounding box 230 in which image information is gathered to learn various details concerning the defect. In order to assure that invalid data from the overlapping area 229 is not included in the data being considered, the center of bounding box 230 is placed at the second image resulting from the dual-line pattern from the linear scanning process of line scan CCD sensor 24.

Figure 14:
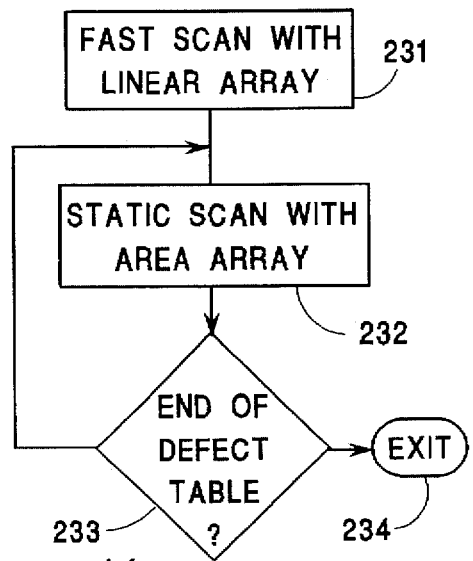
FIG. 14 is a flow diagram showing operation of an overall inspection process according to the present invention.

FIG. 14 is a flow diagram showing the operation of the overall processes of the inspection system. First, as represented in step 231, a fast scan of the disk surface is performed at a constant linear velocity, using data generated from the line scan CCD sensor 24 with the various elements described above in reference to FIGS. 9–12. During this process, a defect table is developed, listing all of the defects found, together with their locations on the list. Following this scan, in step 232, a static scan is performed of each defect in the defect table, using data generated using area array CCD sensor 22 (shown in FIG. 1). When each such static scan is completed, a test is made in step 233 to determine if the end of the defect table has been reached. If it has, the process is exited at 234; otherwise, the next defect from the table is examined in step 232.

Figure 15:
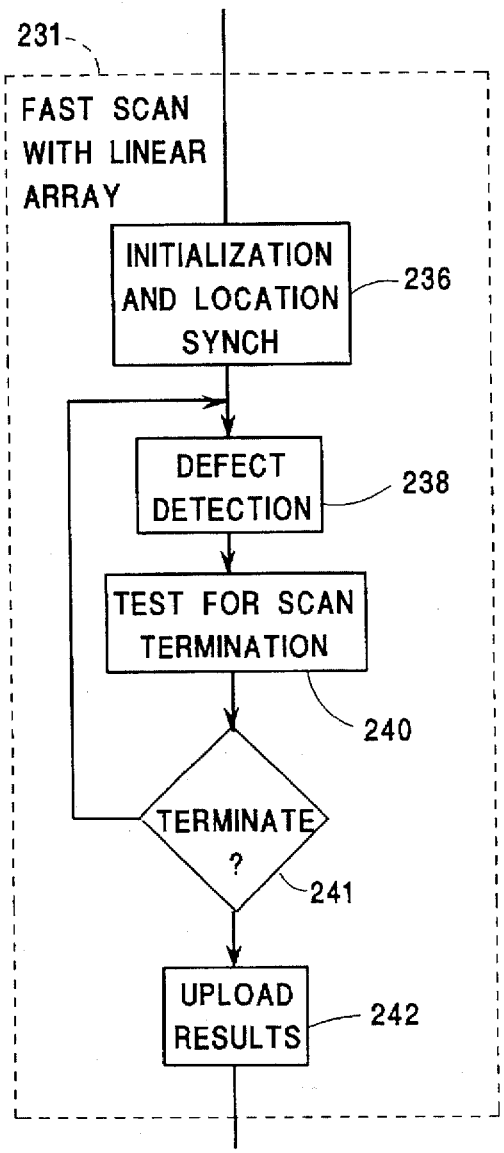
FIG. 15 is a flow diagram showing operation of a fast scan process within the process of FIG. 14.

FIG. 15 is a flow diagram showing the operation of the fast scan process represented in step 231 of FIG. 14. In particular, this Figure provides an overview of the operation of code running in the DSP 168. At the beginning of the fast scan process, in step 236, various circuits are initialized at the starting point of the scan. This initialization process will be discussed in detail in reference to FIG. 16. Then, within the active area of the disk, which is the portion of the disk to be examined, defects are detected in step 238. The defect detection process will be discussed in detail in reference to FIG. 18. In step 240, a test for scan termination is made when processor time is available. For example, scan termination occurs if too many defects have been detected, indicating that the part being tested should be rejected without further testing, or if the detection process has moved off the active area. If scan termination occurs, in step 242, the results of the scan are uploaded to host computer 212 (shown in FIG. 9).

Figure 16:
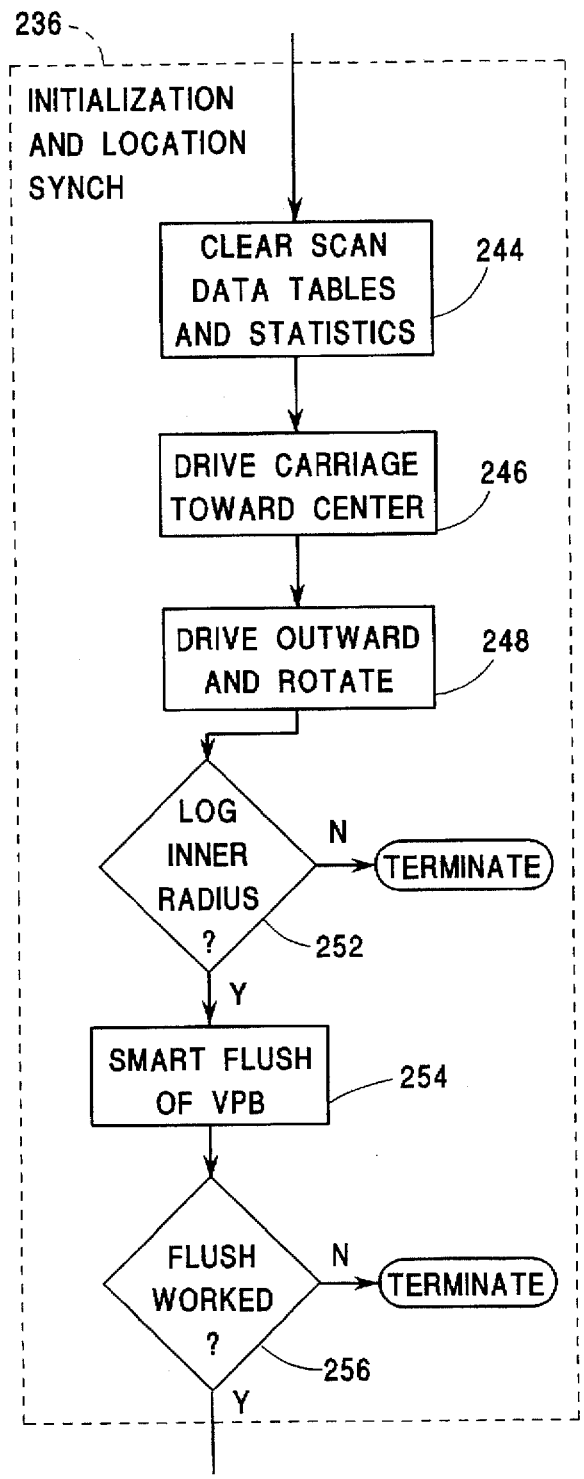
FIG. 16 is a flow diagram showing operation of an initialization and synchronization process within the process of FIG. 15.

FIG. 16 is flow diagram showing the operation of the initialization and synchronization process in step 236 of FIG. 15. Referring again to FIG. 1, as well as to FIG. 16, in step 244, the data tables and statistical values are cleared to eliminate values from a previous fast scan. Then, in step 246, the carriage 159 is driven so that an area toward the center of the disk 157 from the inner radius of the active area is aligned for inspection. In step 248, the spindle 160 is brought up to rotational speed as the stage is driven outward toward a point at which the inner radius of the active area is aligned for inspection. If the inner radius is not logged, the process is terminated at 250 from step 252; otherwise, in step 254 a smart flush is performed on VPB 164 (shown in FIG. 9), resetting variables and synchronizing the operation of the VPB with data flowing into it from the line scan CCD sensor 24. If the smart flush process cannot be completed, as determined in step 256, the overall process is terminated at 258.

Figure 17:
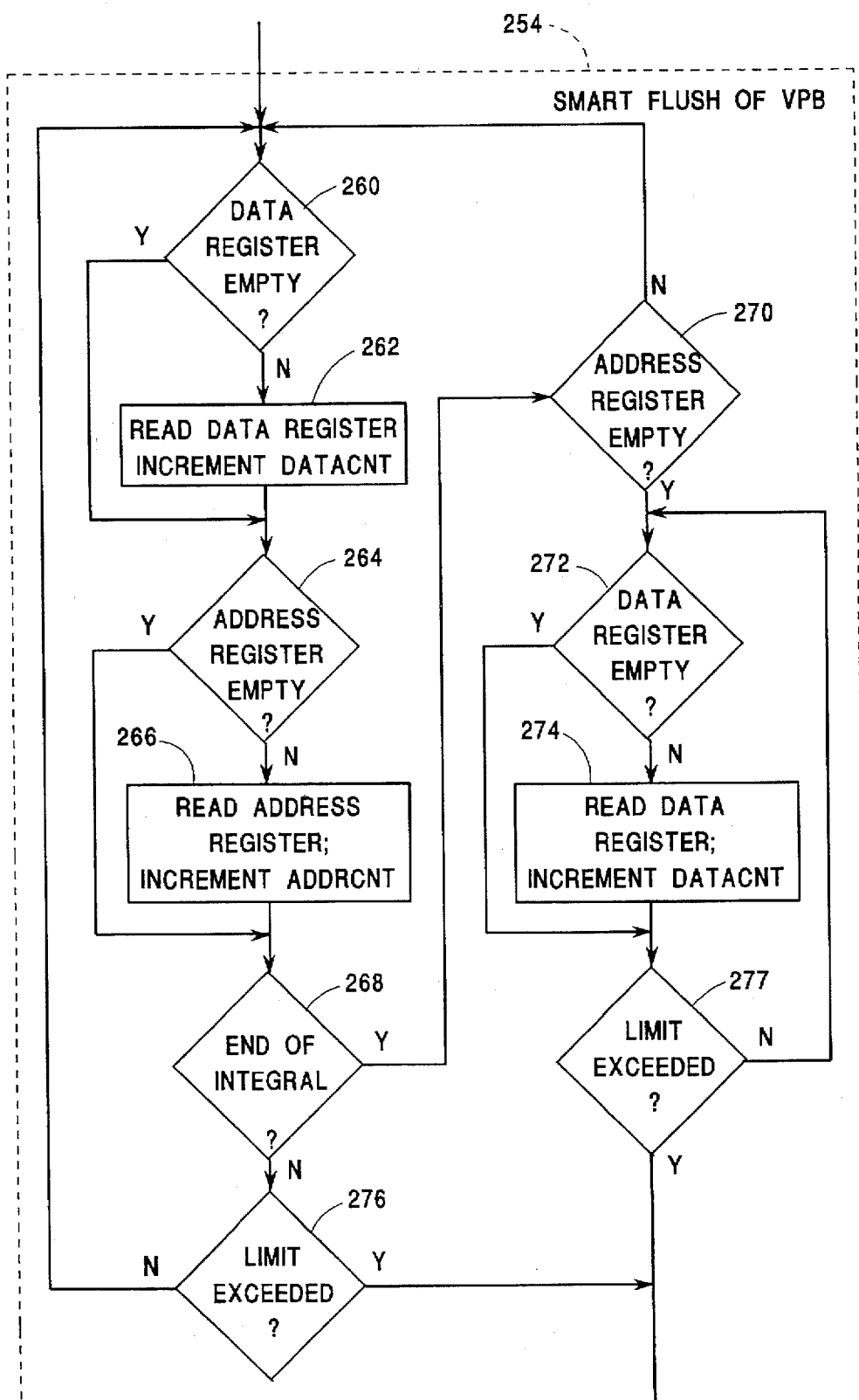
FIG. 17 is a flow diagram showing details of a smart flush process occurring within the process of FIG. 14.

FIG. 17 is a flow diagram showing the details of the smart flush process occurring in step 254 of FIG. 14. In particular, this process clears the FIFO registers described in reference to FIG. 12. In step 260, the last position of data register 195 is checked to determine if it is empty, if it is not empty, this position is read in step 262, and the variable DataCnt is incremented. This variable, if it is at an excessive level, indicates an error condition occurred within the previous operation of the VPB, since the defect detection process of block 238 has not been able to keep up, emptying the data buffer as fast as it has been filled. Next, in step 264, the last position of address register 194 is similarly examined to determine whether it is empty. If it is not empty, this position is read in step 266, and the variable AddrCnt is incremented. This variable, if it is at an excessive level, similarly indicates that an error condition has occurred within the previous operation of the VPB, since the address buffer has not been emptied fast enough. The error conditions indicated by DataCnt and AddrCnt may be caused by a hardware failure, by the beginning threshold level 183 (shown in FIG. 11) being set too low, or simply by an especially bad disk 157 (shown in FIG. 1) displaying too many defects.

In any case, a determination is next made in step 268 of whether an end of integral (video line scan) condition has been indicated by an all-zeros address in address register 194. If an end of integral condition has occurred, the last position of the address register is again checked in step 270. If it is empty, the data register 195 is again checked in step 272. At this point, if the data register is empty, the VPB flush process has been completed, so step 254 is exited. If the data register is not empty, the last value is read in step 274, and DataCnt is incremented. In general, when a determination is made that one of these registers is not empty, the system reads the value and returns to repeat the determination. However, if one of the variables DataCnt or AddrCnt has reached a predetermined limit, as determined by testing at steps 276 and 277, the flush step is also exited, as there is no need to continue.

Figure 18:
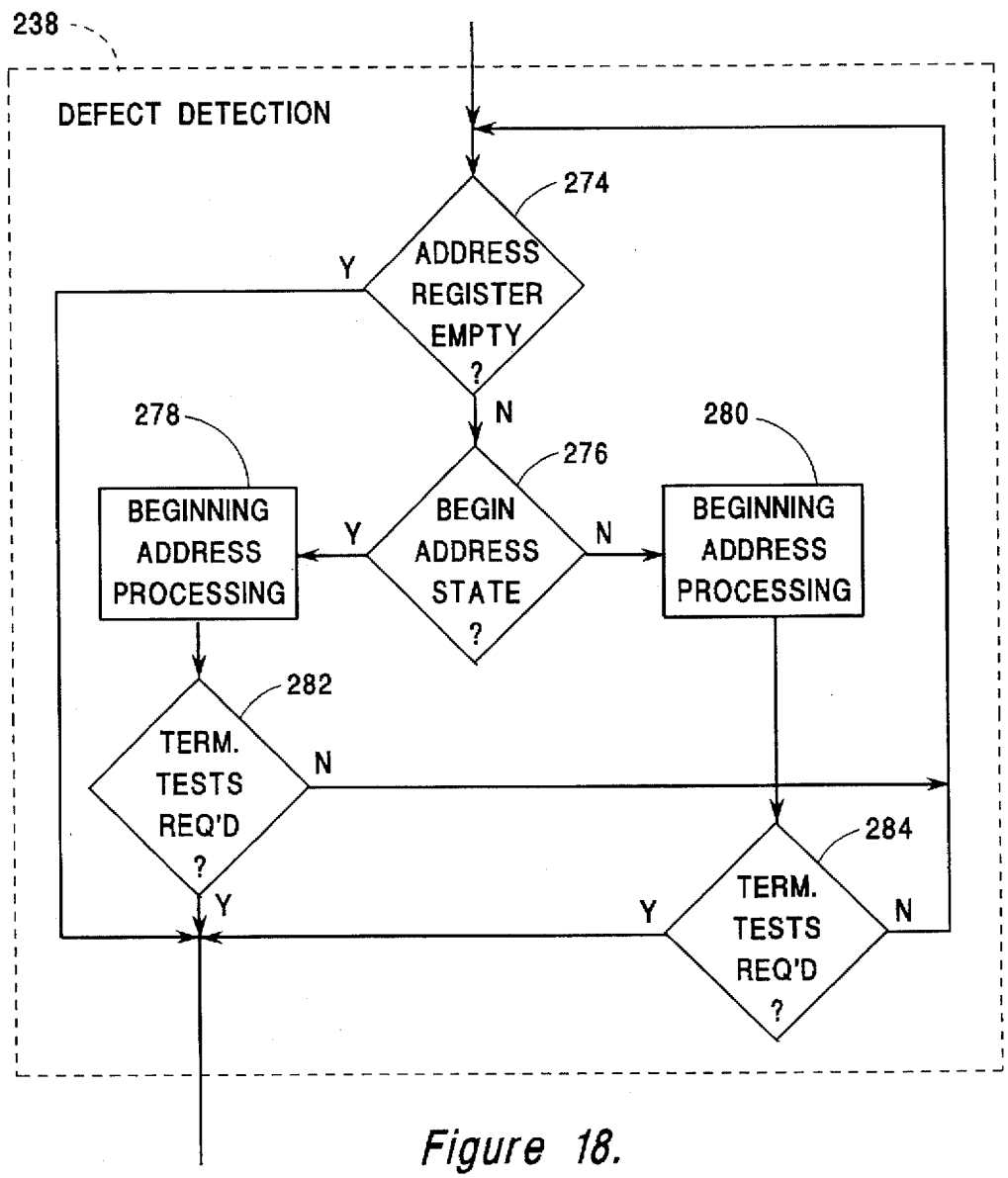
FIG. 18 is a flow diagram showing operation of a defect detection process occurring in the process of FIG. 15.

FIG. 18 is a flow diagram showing the operation of the defect detection process occurring in step 238 of FIG. 15.

This is a process through which the DSP 168 (shown in FIG. 9) examines each defect for which data has been stored in the FIFO registers 194 and 195 (shown in FIG. 12). In step 274, a determination is made of whether the address register 194 is empty. If it is, there is no defect to detect, nor end of integral marker to process, so address processing is bypassed. Next, a determination is made, in step 276, of whether the next data in the address register 194 is a beginning address. After an End of Integral code, the next address (unless it is another line integral code) must be a beginning address. After a beginning address, the next address must be an ending address. From this point, the type of address toggles between beginning and ending, until an End of Integral code is reached. If the address is determined in this way to be a beginning address, the beginning address processing, which will be is explained in detail in reference to FIG. 19, occurs in step 278. If the system is not in the beginning address state, ending address processing, which will be explained in detail in reference to FIG. 20 occurs in step 280. Referring again to FIG. 15, following the defect detection process, a test is made, in step 240, for scan termination. Thus, following beginning address processing in step 278, a test is made in step 282 to determine if the update count is at its limit. If it is, terminal testing is needed, so the system exits the defect detection process of step 238. If the update count is not at its limit, the address register is again checked at step 274, for the next data point. Similarly, after the ending address processing of step 280, a determination is made in step 284 of whether the defect table is full. If it is, terminal testing is needed, so the system exits the defect detection process of step 238. If the defect table is not full, the address register is again checked at step 274, for the next data point.

Figure 19:
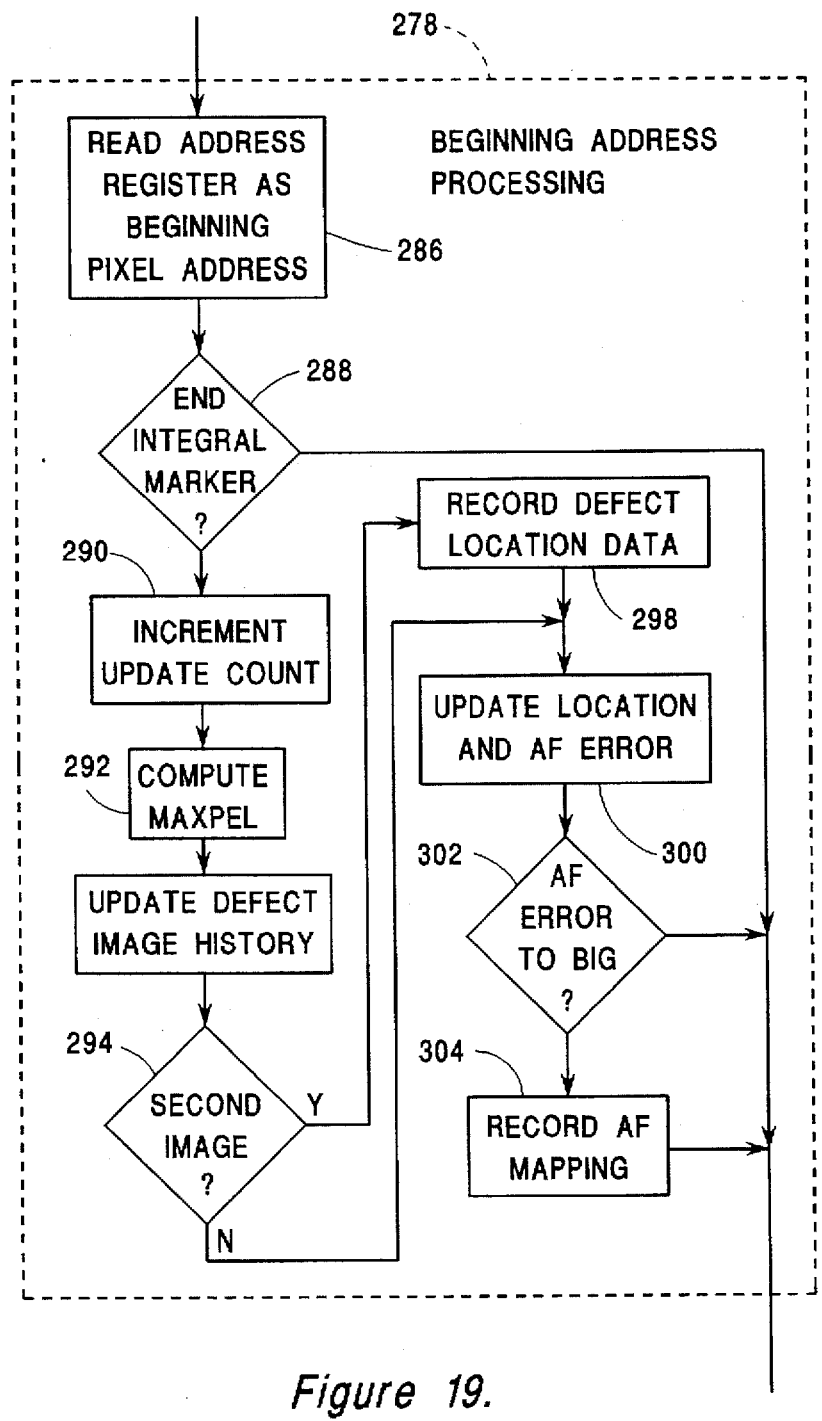
FIG. 19 is a flow diagram showing operation of beginning address processing occurring in the process of FIG. 18.
Figure 21:
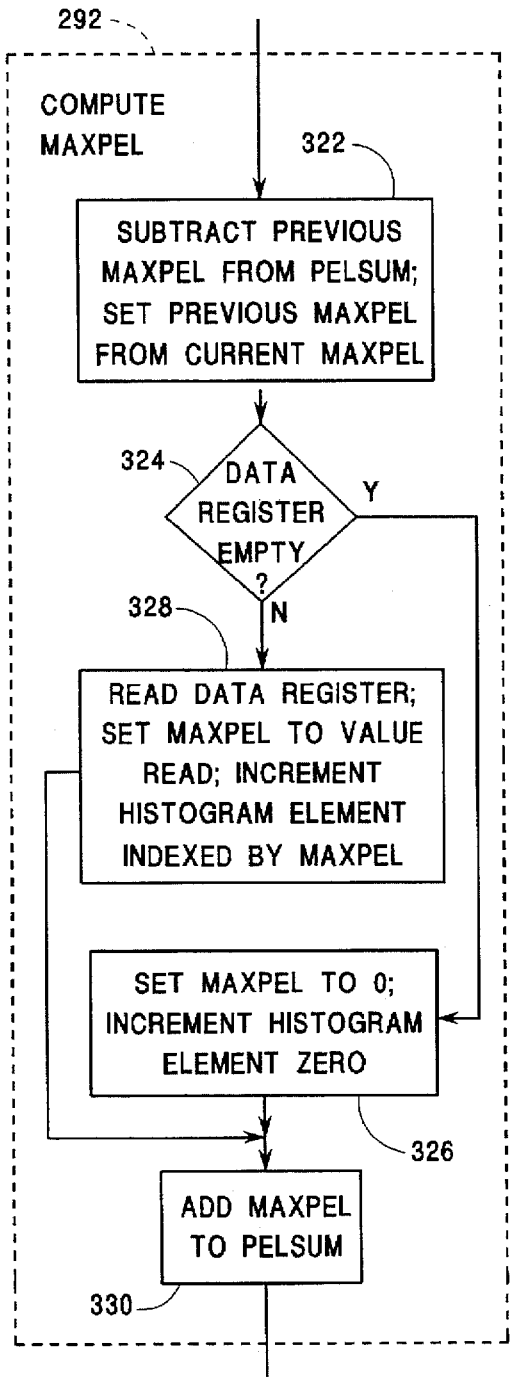
FIG. 21 is a flow diagram showing a process implemented within the process of FIG. 19 to handle a condition in which a defect extends between sequentially adjacent integrals.

FIG. 19 is a flow diagram showing the operation of the beginning address processing process occurring in step 278 of FIG. 18. In step 286, the Address register 194 (shown in FIG. 12) is read to obtain the beginning pixel address. If the End of Integral marker is not present, the system has detected the start of a defect within the integral and stored this starting address, so that beginning address processing is exited. Otherwise, the beginning address processing continues with the Update Count being incremented in step 290. Next, in step 292, a provision, which will be explained in detail in reference to FIG. 21, is made for handling the condition in which a defect extends from one pixel to another. Then, the Defect Image History is updated in step 294, in a manner which will be explained in detail in reference to FIG. 22.

As previously described in reference to FIG. 13, to obtain valid results, it is necessary to center the static scan CCD sensor 22 on the second image resulting from each defect. This is achieved by listing only the address of the second image with various data collected during the linear scanning process. Thus, within beginning address processing, a check is made in step 296 to determine whether the current image is the second image of a defect. With the typical integration length of 30 microns, the second image is two integrals (or video scans) behind a similar first image. If the current image is determined to be the second image, the defect location is recorded with associated data in step 298. Whether the image is the first or second image, the data indicating the position (radius and angle) being inspected is updated, along with the autofocus data and prism position data, in step 300. If the new autofocus position differs from its previously logged position by a pre-determined threshold limit, as determined in step 302, autofocus mapping, along with positional and phase angle data occurs in step 304. Next, beginning address processing is exited.

Figure 20:
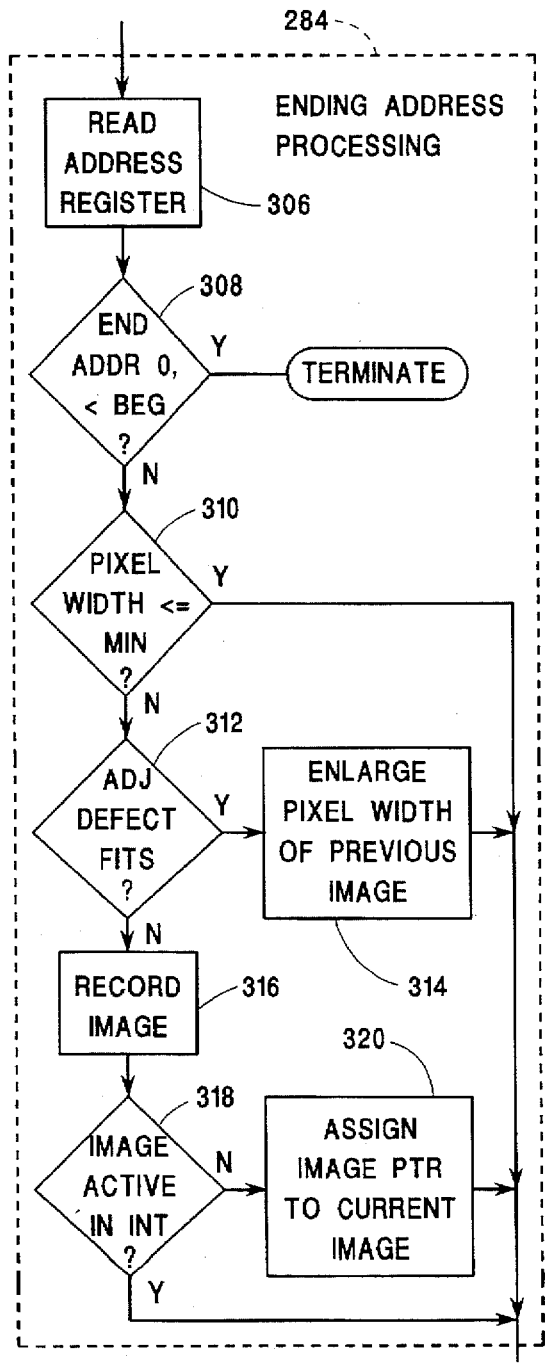
FIG. 20 is a flow diagram showing operation of ending address processing occurring in the process of FIG. 18.

FIG. 20 is a flow diagram showing the operation of the ending address processing occurring in step 284 of FIG. 18. The address register 194 is read in step 306, and a check for error conditions is made in step 308. Specifically, if the ending address is determined to be equal to zero or less than the current beginning address, a hardware error has occurred in VPB 164, so processing is terminated. Next, in step 310, a check is made to determine if the pixel width is less than a preset minimum, If it is, the processing of this particular ending address is exited. Next, in step 312, it is determined whether the adjacent defect image and the current image will fit within the bounding box used for static scanning with CCD sensor 22. If they will not fit, this ending address processing is exited after the pixel width of the previous image is enlarged in step 314. Otherwise, in step 316, the image data is recorded, including pixel addresses, the position (radius and angle) the autofocus and prism location settings, and the integral count. Then, in step 318, a determination is made of whether another image is already active within this integral. If it is not, an active image pointer is assigned to the current image in step 320. In either case, ending address processing is exited.

FIG. 21 is a flow diagram showing the process of step 292 in FIG. 19, which is implemented to handle the condition in which a defect extends between sequentially adjacent integrals. In the absence of this type of provision, this condition presents the possibility of having a defect, which should be detected, but which is nevertheless not detected because, it contributes a portion of its resulting intensity to two integrals without raising the intensity of either of them to a level which is detected. To prevent this problem, a summed intensity, called PelSum is calculated for each sequentially adjacent pair of integrals, being determined for stored data in the form of the previous PelSum value, and from the current maximum intensity level, current MaxPel. In order to determine a new value for PelSum, in step 322, the previous value of MaxPel is subtracted from PelSum, and the Previous MaxPel is set to the level of the current MaxPel.

One of the forms of data being developed during this process is a histogram having elements corresponding to the various detected intensity values of MaxPel. Each time a value of MaxPel is determined, the histogram element indexed by the MaxPel value is incremented. In step 324, data register 195 is examined to determine if it is empty. It should not be empty, but if it is, in step 326, MaxPel is set to zero, and the histogram element 0 is incremented, indicating that a problem has occurred. If data is available from data register 195, in step 328, this value is read, and the histogram element indexed by this value is indexed. Finally, the new value for MaxPel is added to PelSum in step 330.

Figure 22:
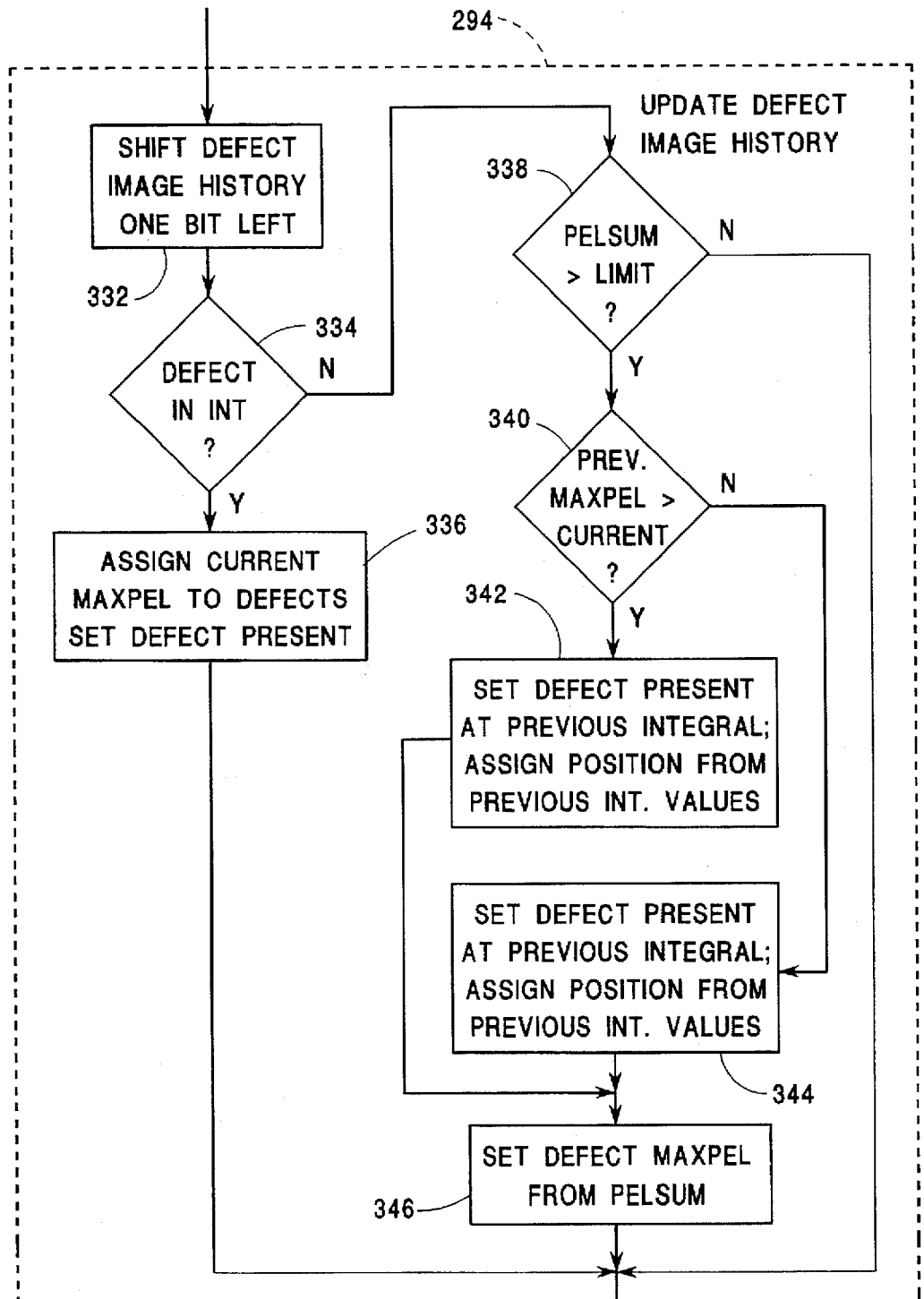
FIG. 22 is a flow diagram showing a process updating the defect image history table within the process of FIG. 19.

FIG. 22 is a flow diagram showing the process of step 294 in FIG. 19, in which the Defect Image History table is updated. First, in step 332, this table is shifted one bit to the left. Then, in step 334, it is determined if another active image is already in the current integral. If it is, in step 336, the current MaxPel is assigned to active defects in the integral, a defect present bit is set in the image history, and the current Defect MaxPel is set to the current MaxPel, and this step 294 is exited. On the other hand, if an active image is not already in the integral, as determined by step 334, a determination is made in step 338 of whether PelSum is above the beginning threshold 183 (shown in FIG. 11). If PelSum is not above this threshold, a defect is not considered detected, and this step 294 is exited. If PelSum is above this threshold level, a new defect is set, either in the current integral or in the previous integral, depending on which has the greatest MaxPel value. thus a determination is made in step 340 of whether the previous MaxPel is greater than the present MaxPel. If the previous MaxPel is greater, in step 342, the Defect Present Bit is set in the Image History at the position corresponding to the previous integral., and defect position (radius and angle) values, an autofocus value, and a prism position value are assigned from the levels associated with the previous integral. If the current MaxPel is greater, in step 344, the Defect Present Bit is set at the position corresponding to the present integral, and these values are assigned the levels of the current integral. In either case, the Defect MaxPel is set from the PelSum in step 346, and the updating process of step 294 is exited.

Figure 23:
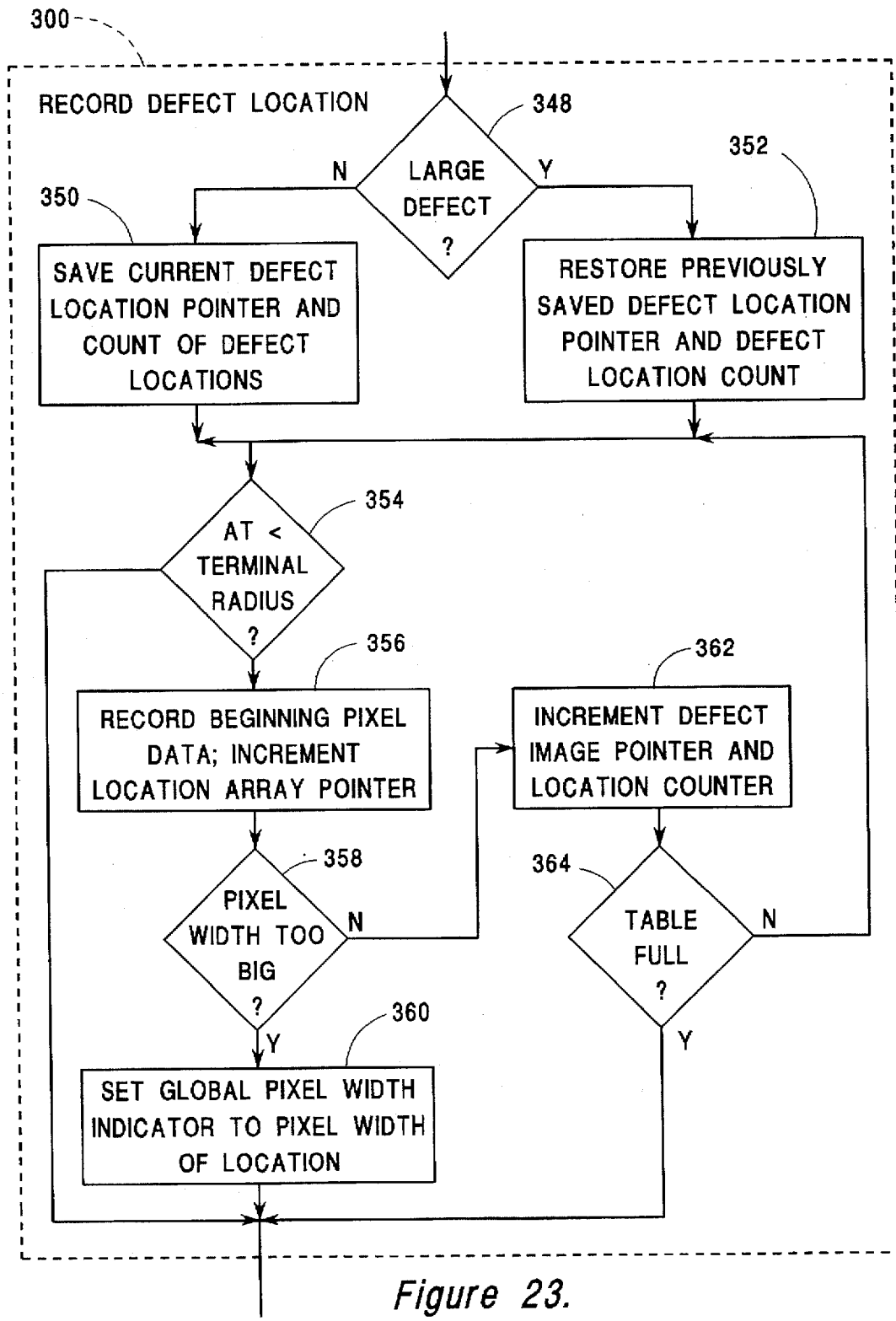
FIG. 23 is a flow diagram showing a process of recording a defect location in the process of FIG. 19.

FIG. 23 is a flow diagram showing the process of step 300 in FIG. 19, in which the defect location is recorded. First, a determination is made in step 348 of whether the defect being detected is a portion of a larger defect which has already been detected. If it is not part of a larger defect, as determined by looking at the results for the previous integral, the current Defect Location Pointer and the present Count of Defect Locations is saved in step 350. If it is part of a large defect, the previously saved Defect Location Pointer and the previous Defect Location Count are saved in step 352. In this way, only the defect image of the last integral is recorded for defects which span adjacent integrals.

Referring again to FIG. 13, the need for this procedure is illustrated by considering the interferogram pattern 354 caused by a large defect. When such a pattern is viewed in the static scan process by array CCD sensor 24, if the large defect is located to extend downward from the center of bounding box 230, all of the image of the large defect within the bounding box consists of a valid positive image. If the bounding box is instead moved downward along the interferogram of the large defect, both positive and negative images will be present within the bounding box, producing invalid or indeterminant results.

Referring again to FIG. 23, if there is a defect image to record, and if the radial location of the defect is less that the terminal radius indicating the defect is within the active region being examined, as determined in step 354, defect data is recorded in step 356. Specifically, the beginning pixel address and width are recorded, along with the Defect MaxPel, location data, antofocus and prism location data, and the integral counter. The location of the Defect Location Array Pointer is also incremented. Next, a determination is made in step 358 of whether the defect is too wide, exceeding a maximum pixel width threshold. If it is too wide, in step 360, the global pixel width indicator is set to the pixel width of the location. If it is not too wide, in step 362, the Defect Image Pointer and Location Counter are incremented. Then if the Defect Location Table is full, as determined in step 364, the process of recording defect locations is exited. If this table is not full, the next defect in this integral, if there is one, as determined in step 345, is examined for recording.

Figure 24:
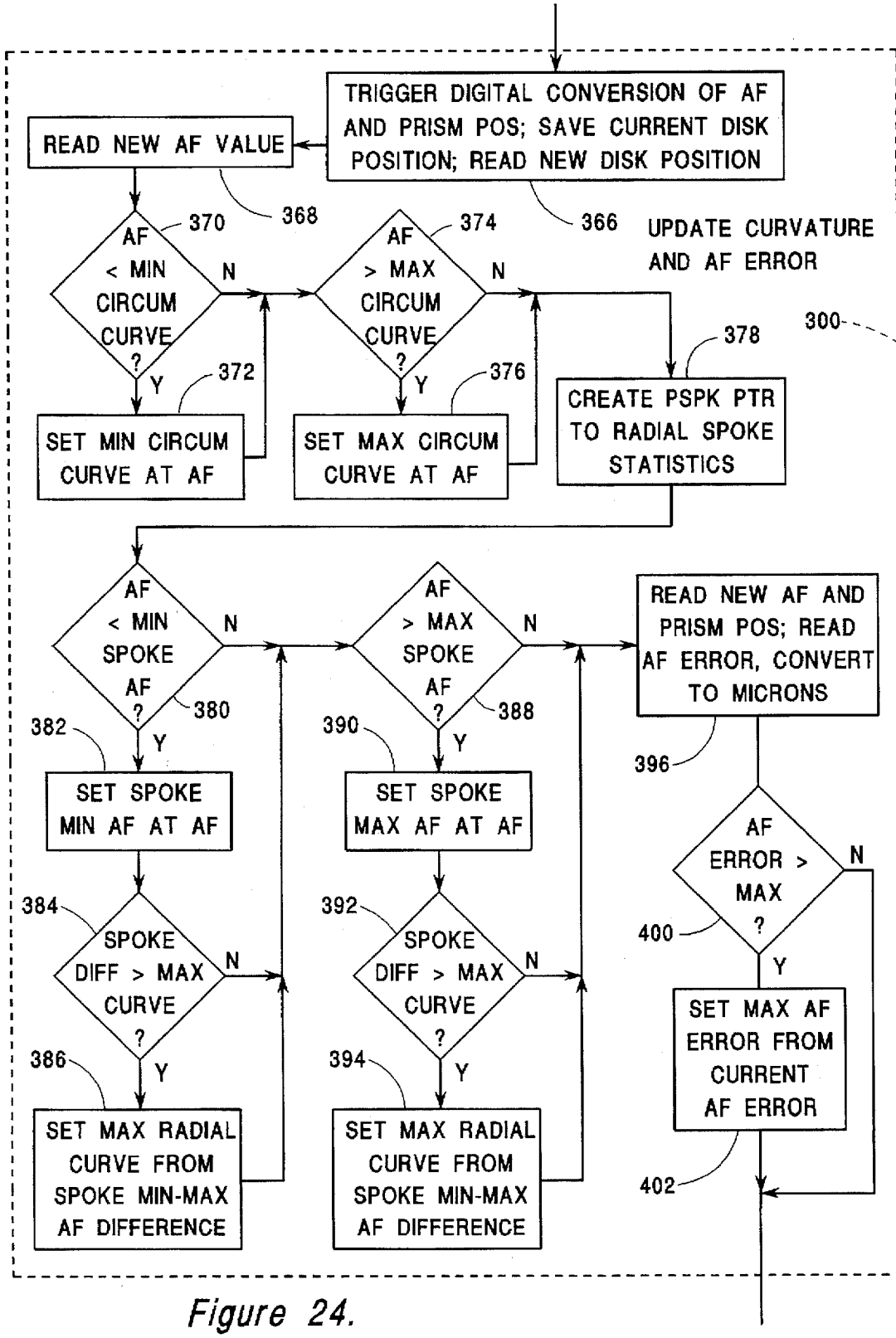
FIG. 24 is a flow diagram showing the operation of a record autofocus mapping step in the process of FIG. 19.

FIG. 24 is a flow diagram showing the operation of the record autofocus mapping step 304 in FIG. 19. In autofocus mapping, the current autofocus value is used to set circumferential and radial curvature characteristics describing certain features of the disk being tested. First, in step 366, the analog to digital conversion of autofocus and prism position signals is triggered, current position variables (radius and angle) are stored as previous, and new current position variables are read. Next, in step 368, a new autofocus value is read. This autofocus value is used to set or reset maximum and minimum values of a circumferential curvature variable indicating the flatness of the disk 157 being tested. If it is determined in step 370 that the autofocus value is less than the minimum circumferential curvature, the minimum circumferential curvature is set to the current autofocus value in step 372. If it is determined in step 374 that the autofocus level is greater than the maximum circumferential curvature, the maximum circumferential curvature is set to the autofocus value in step 376.

Next, in step 378, a spoke pointer, pSpk is created to allow the development of spoke statistics along a spoke, which is defined as a line extending outward from the center of the disk at the current angle. If it is determined in step 380 that the current autofocus value is less than the minimum autofocus for the spoke, in step 382 the spoke's minimum autofocus value is set from the current autofocus value. If it is determined in step 384 that the minimum to maximum autofocus difference is greater than the maximum radial curvature for the disk, in step 386 the maximum radial curvature is set from the minimum to maximum autofocus difference. If it is determined in step 388 that the current autofocus value is greater than the maximum autofocus value for the spoke, this latter value is set at the current autofocus value in step 390. If it is determined in step 392 that the minimum to maximum autofocus distance is greater than the maximum radial curvature for the disk, the maximum radial curvature is set from the minimum to maximum autofocus distance of the spoke in step 394. Next, in step 396, current values are read for the autofocus (lens position) and for the prism position. The codes for these variables are formed into a pair for storage.

As previously described in reference to FIG. 1, a differential error signal indicating the focusing error, experienced in the subsystem for automatically focussing the lens 20, is generated within controller 122 from the difference between the outputs of photodetectors 144 and 146. Since this error signal represents the ability of the autofocus signal to keep up with changes in the height of the disk 157 as it is moved for inspection, and thereby to keep the interferometer 10 functioning properly, this error signal is also read in step 396, to be converted into an equivalent autofocus error in microns. Next, in step 400, the current autofocus error is compared with the currently stored maximum autofocus error. If the current autofocus error is greater, the maximum autofocus error is set to the new maximum level in step 402. In either case, the step 304 is next exited.

Figure 25:
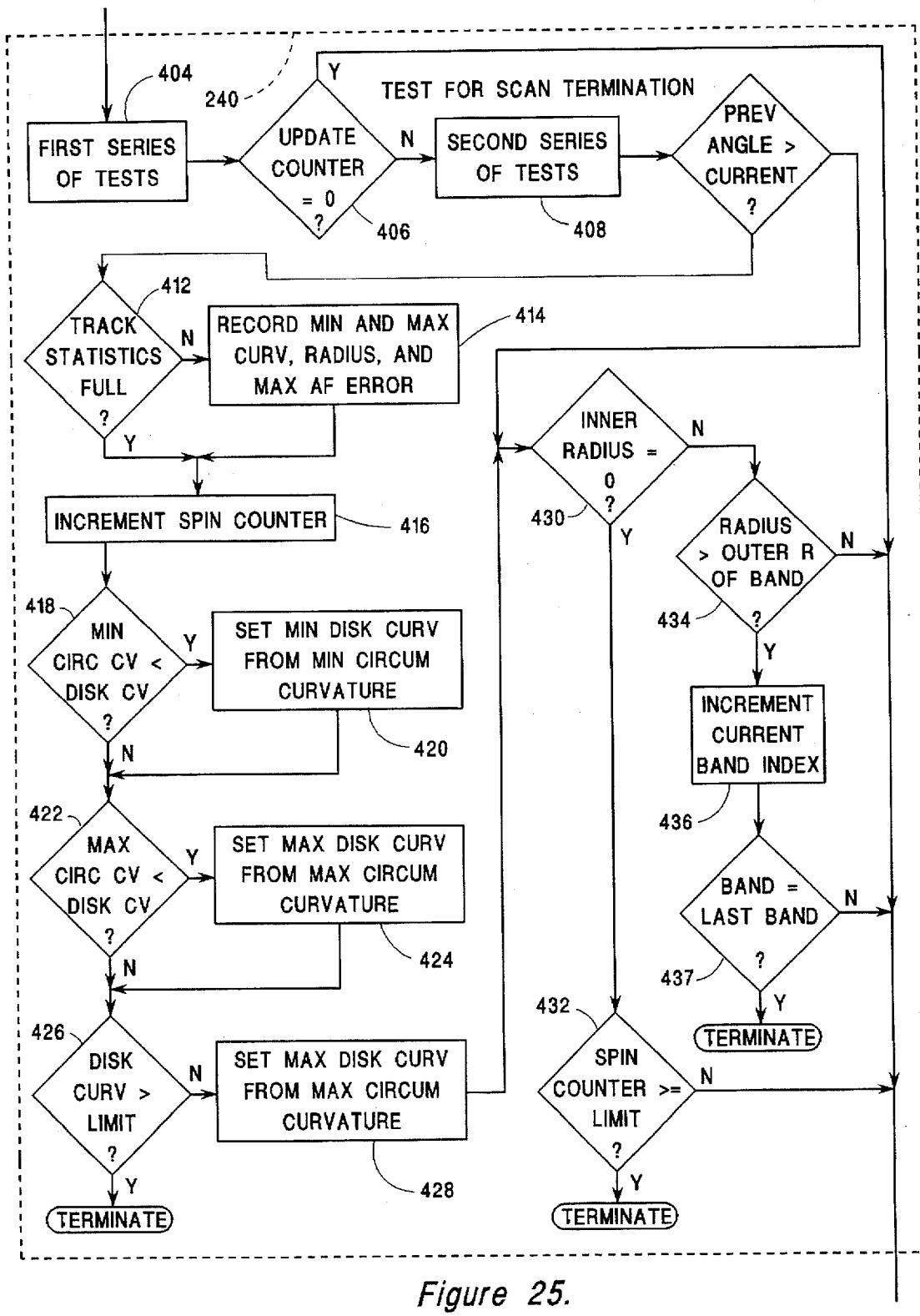
FIG. 25 is a flow diagram showing processes occurring in the test for scan termination within FIG. 15.

FIG. 25 is a flow diagram showing the processes occurring in the test for scan termination of step 240 in FIG. 15. In a first series of tests occurring in step 404, a terminate condition is determined if the defect image table is full, if the defect location table is full, if the autofocus map table is full, if the pixel width exceeded a limit, if the scan time exceeded a time-out limit, if the address buffer 194 is full and latched, or if the data buffer 195 is full and latched. If any of these terminate conditions is met, the inspection process is terminated. The effect of termination is shown in FIG. 15. Next, in step 406, the Update Counter is tested to see if it equals zero. If it equals zero at this point, it has been set to zero at the start of the defect scan, so the scan termination testing is exited. In a second series of tests occurring in step 408, a number of other termination conditions are checked. The process is terminated if the current angle is greater than the maximum (360 degree) angle, indicating that the spindle encoder 198 (shown in FIG. 9) counted too many bits, if the Defect Image Count exceeds the Limit in Band (which is a pre-determined maximum number of defects allowable in an annular portion of the disk 157), if the circumferential curvature exceeds the Limit in Band (which is a pre-determined maximum allowable curvature within an annular portion of the disk), or if the maximum radial curvature exceeds the Limit in Band.

Next, in step 410, a determination is made of whether the previous angle is greater than the current angle. If it is, a full revolution has been completed by the spindle 160 (shown in FIG. 1), passing the 0-degree angle indicating the start of a new revolution. If this has occurred, a number of operations occurring at the end of a full revolution are performed. First, a test is performed in step 412 to determine if the Track Statistic Array is full. If it is not full, various statistics for the track—minimum and maximum curvature, radius, and maximum autofocus error—are recorded in step 414. In either case, the spin counter is incremented in step 416, and a test is made in step 418 to determine if the minimum circumferential curvature is set at a value less than the disk curvature. If it is, in step 420, the minimum disk curvature is set at the level of the minimum circumferential curvature. Similarly, a test is them made in step 422 to determine if the maximum circumferential curvature is set at a value less than the disk curvature. If it is, the maximum disk curvature is set to the level of the maximum circumferential curvature in step 424. Next, in block 426, a determination is made of whether the disk curvature exceeds the Limit in Band. If it does, the process is terminated; otherwise, in step 428, the maximum disk curvature is set from the maximum circumferential curvature.

On the other hand, if it is determined in step 410 that a complete revolution has not been completed, the various processes described above as following step 410 are not required. In either case, in step 430, a determination is made of whether the inner radius is zero. If it is, it is known that the inner radius has been set to zero to perform a special diagnostic procedure in which the spindle 160 is rotated without moving the carriage 159 (both shown in FIG. 1). In such a test, the number of rotations desired is initially set as a limit; so if the inner radius is zero, in step 432, the spin counter is checked against this limit. If the limit has been reached, the process is terminated, as it has been completed; otherwise the test for termination step 240 is exited.

If it is determined in step 430 that the inner radius is not zero, a full-disk inspection is in progress. The concept of bands has been implemented to allow variations in inspection criteria for different bands, or annular areas, within the active area of the disk. Thus, in step 434, the radial position of carriage 159 is compared to the outer radius of the current band. If the current radius is not greater than the outer radius of the band, the test for termination step 240 is exited. If the current radius is greater than the outer radius of the current band, the current band index is incremented in step 436. If the new current band is equal to the max band limit, as determined in step 438, the test is terminated, as it has been completed; otherwise the test for termination is exited.

Figure 26:
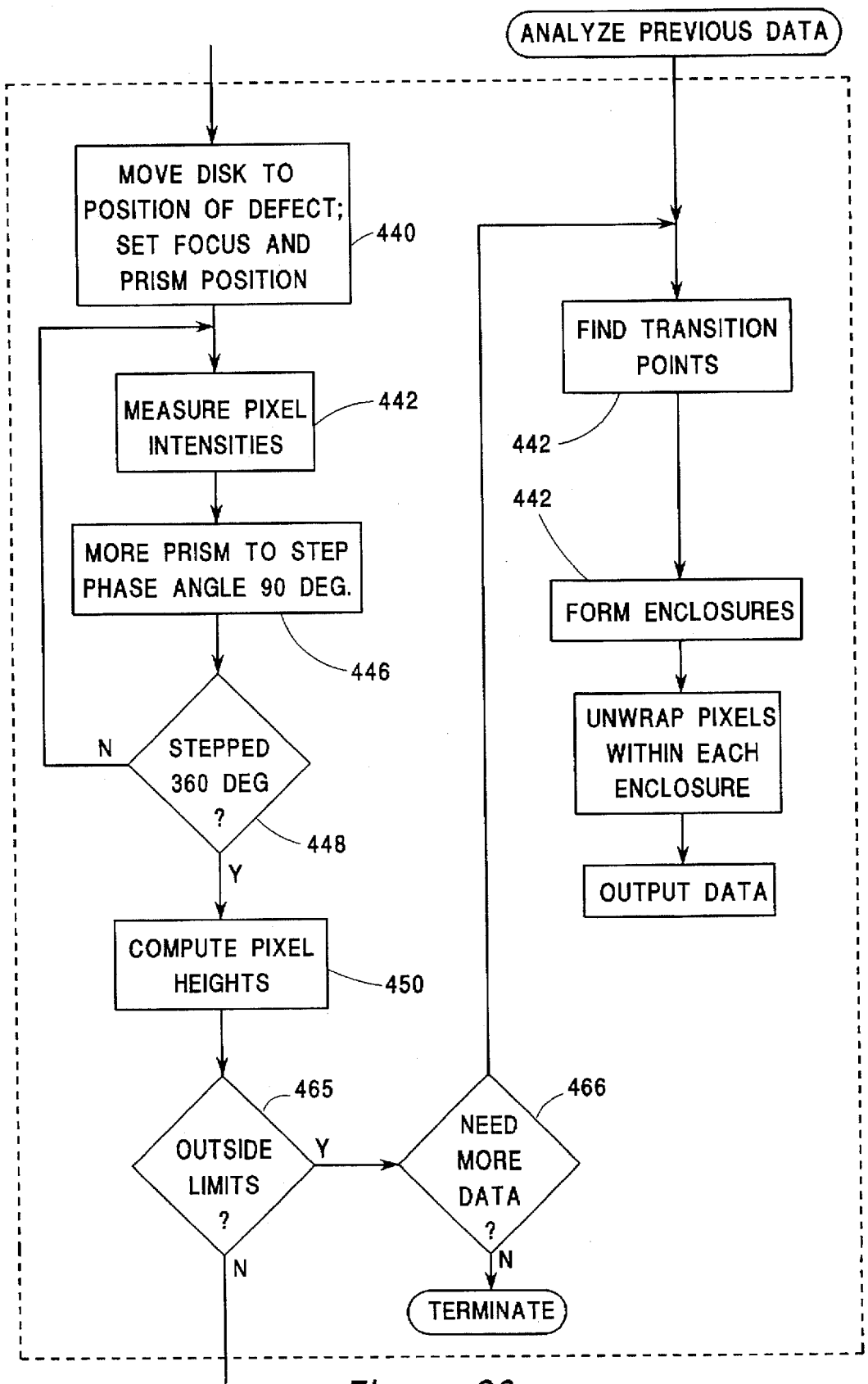
FIG. 26 is a flow diagram showing processes occurring as a static scan is performed in the process of FIG. 14.

FIG. 26 is flow chart describing the processes which occur in step 232 of FIG. 14. In this step, a static scan is performed to determine the precise characteristics of a defect previously detected by the fast scan process of step 231 is performed. This step 232 is repeated for each entry in a Defect Table, which lists the defects determined to be present in a particular disk 157 (shown in FIG. 1) being tested.

Thus, referring to FIGS. 1 and 26, in step 440, for the current defect being examined, the carriage 159 and spindle 160 are set to the locations stored during the fast scan process of step 231. Similarly, the focussing location of lens 20, which has been stored for the defect is used to move lens 20 into focus using piezoelectric actuator 141. Also, the position of Wollaston prism 18, which has similarly been stored for the defect is used to move the prism 18 into the position needed for darkfield conditions, through the operation of piezoelectric actuator 126. Next, in step 442 the two-dimensional image of the defect is acquired. This image consists of an intensity level for each of the pixels in the interferogram measured by area CCD array 24. Next, in step 444, the Wollaston prism is moved with piezoelectric actuator 141 to shift the phase angle of the interferogram by 90 degrees. For example, when the phase angle has been shifted twice in this way, through a 180-degree angle from the darkfield conditions, a brightfield interferogram is introduced. For each of these positions, an interferogram is acquired in step 442.

After the phase angle has been shifted a full revolution, as determined in step 448, the height represented by each pixel is calculated, in step 450, by the following equation:

$$h = \frac{\lambda}{4\pi} \arctan \frac{I_3 - I_1}{I_2 - I_0}$$

where h represents the calculated height, I represents the intensity measured for each pixel at the phase angle identified by the subscript, with 0 representing 0 degrees (darkfield), 1 representing 90 degrees, 2 representing 180 degrees (brightfield) and 3 representing 270 degrees. The wavelength of the light produced by the laser, in the present example 532 nanometers, is represented by $\lambda$. The sign of the arctan term determines whether the area represented by a particular pixel is depressed below or raised above the plane at which darkfield conditions are established. If the height of a pixel is more than a quarter wave length ($\lambda/4$) above or below this plane, it appears at a level within a quarter wave length of this plane, having had an integral number of half wave lengths ($\lambda/2$) added or subtracted from its actual height as needed to meet this condition.

Figure 27:
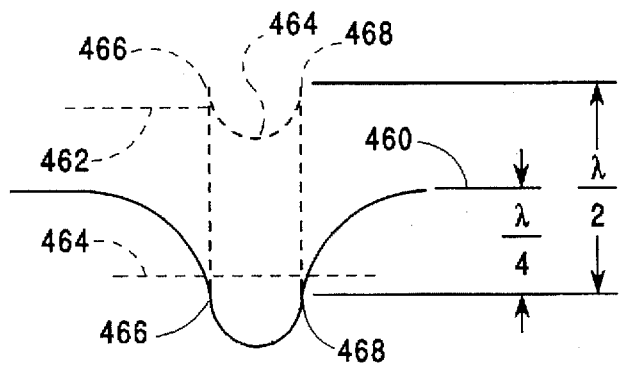
FIG. 27 is a graphical view of a graphical cross-sectional view of a defect in a test surface, as determined by the static scan of FIG. 26.

FIG. 27 is a graphical view of the cross section of a defect. The solid line 458 represents the actual shape of the defect, which is followed by values calculated according to the equation of the preceding paragraph within a quarter wave length of the darkfield plane 460. In this example, when the actual shape of the defect falls below a quarter wave length distance, indicated by line 462, the apparent height values indicated by dashed line 464, calculated according to the equation, are a half wave length above the actual values.

Referring again to FIG. 26, and continuing to refer to FIG. 27, in a typical manufacturing inspection application, the maximum height limit 462 and the maximum depth limit 464 for an allowable defect are each within a quarter wave length of the darkfield plane 460. Thus, when the calculated height of a pixel falls outside these limits, as determined in step 464, and if no more information is needed, as determined in step 466, the process is terminated, as the part being inspected is rejected. On the other hand, if no defect falls outside the limits 462 and 464, the static scan step 232 is exited. From this point, as shown in FIG. 14, the static scanning process is repeated until all of the defects in the defect table have been examined.

In other cases, it is desirable to continue processing the data, determining the actual characteristics of the defect, in order to make improvements to the manufacturing process. In any case, the limits 462 and 464 may be used to determine whether an unwrapping process should be applied to determine the actual height of pixels which fall outside the limits. Thus, from step 464, if the system is being operated in an investigational mode, in which more data on defects falling outside the limits is required, a phase unwrapping process is entered in step 468.

Continuing to refer to FIG. 27, a pair of transition points 466 occur wherever the actual height of a defect surface moves outside the quarter wave length limit 462. These transition points are characterized by a change in sign, indicating a reversal in the direction of displacement from the darkfield plane 460, and by a relatively large change in the level from one pixel to an adjacent pixel. For example, such a transition can be assumed to occur whenever, between two adjacent pixels, there is a change in sign and an absolute change of over 100 nanometers.

In the unwrapping process a line of such transition points is traversed, hopefully to find a figure enclosing a surface falling outside the quarter wave length limits. When such a surface is found a distance of a half wave length is added to, or subtracted from, the previously-calculated height values. Whether to add or subtract is easily determined from the direction at which the rapid height change occurs. In the example of FIG. 27, a rapid upward change occurs during scanning to the right, between the pair of transition points 466. It is thus evident that a half wave length should be subtracted from the calculated heights of points in the area to the right of these transition points 466. With further scanning to the right, a pair of transition points 468, indicating a sharp downward transition from left to right, is encountered. It is therefore evident that the half wave length distance should no longer be subtracted from the calculated heights.

Figure 28:
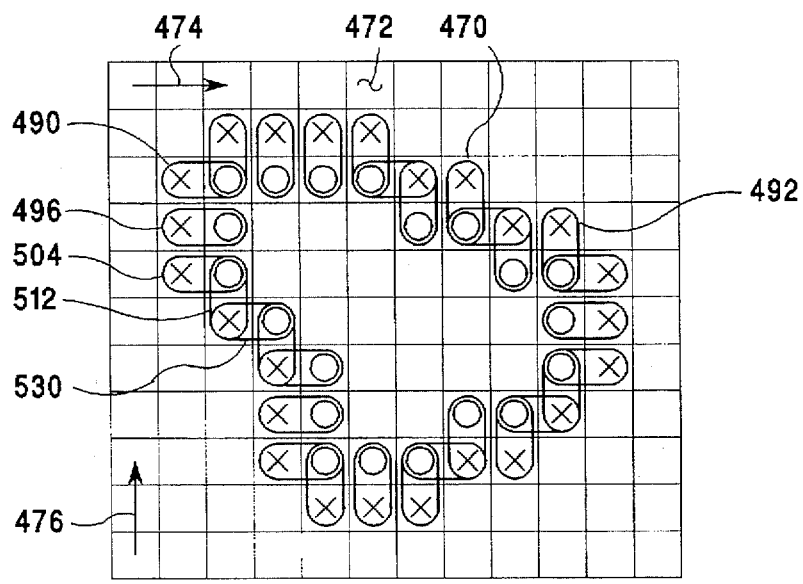
FIG. 28 is a schematic representation of a transition table formed from data developed in the static scan of FIG. 26.

FIG. 28 is a schematic representation of a transition table, in which each pair of transition points is identified by an oblong FIG. 470. Each element 472 in this table represents a pixel. In this example of a depression, the letter X represents the pixel on the low side of the transition, while the letter O represents the pixel on the high side of the transition.

Figure 29:
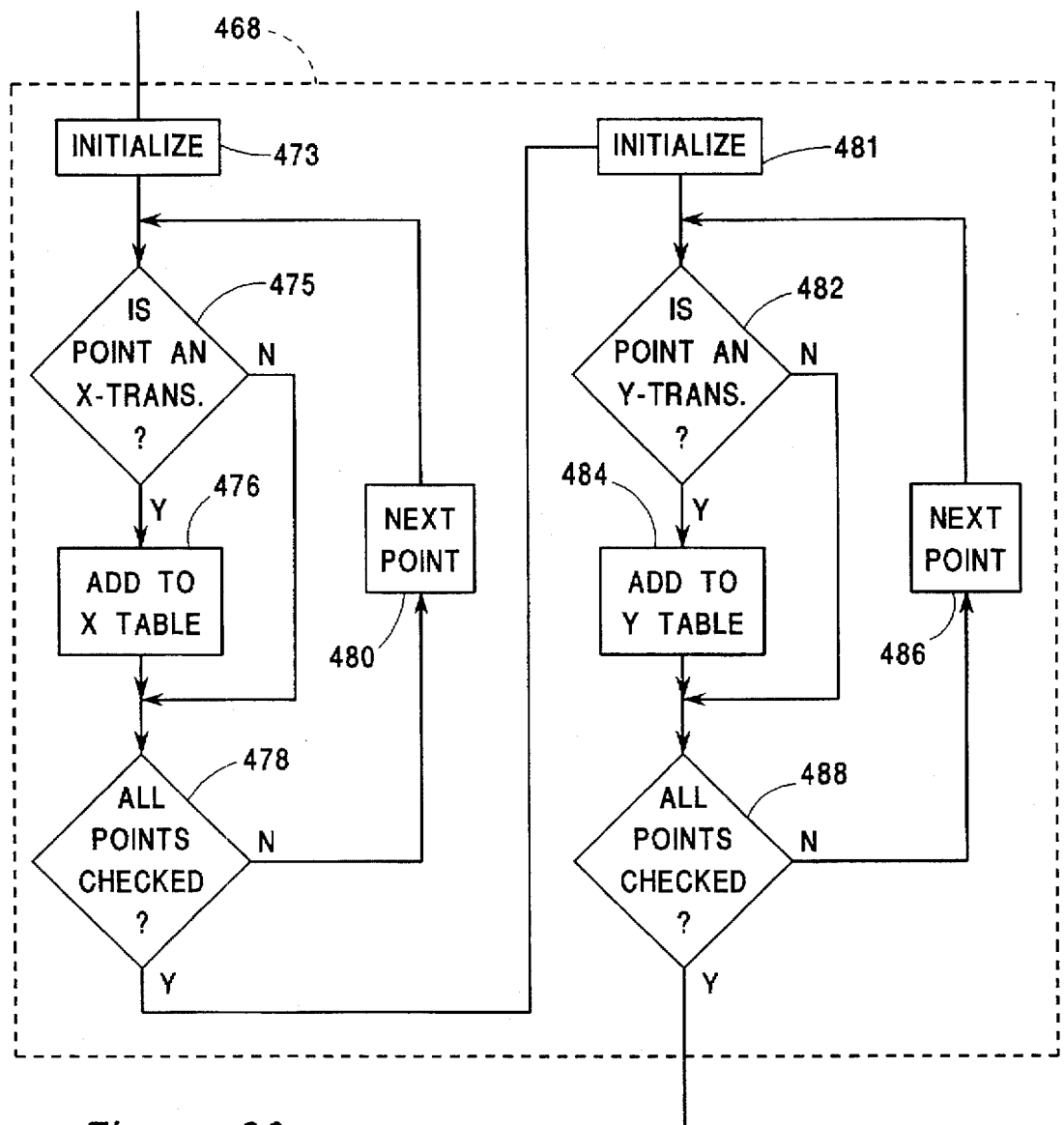
FIG. 29 is a flow diagram of the processes occurring in a first step of an unwrapping process within the processes of FIG. 26.

FIG. 29 is a flow diagram of the processes occurring in a first step 468 of the unwrapping process, in which tables of X- and Y-transition points are generated. In the first part of this process, the table of heights, calculated according to the equation given above, is traversed in the X-direction of arrow 474. When the end of each row is reached, the next row is traversed, until all the rows have been completed. In step 474, a determination is made of whether a point is an X-transition point by comparing it with the preceding point, according to the pre-established criteria. For example a point and its preceding point are considered to be an x-transition pair if they differ in sign and in value by more than 100 nanometers. In step 476, each X-transition point is added to an X-transition table. Next, in step 478, a determination is made of whether all points have been checked. If they have not all been checked in this way, the next point is selected in step 480, and the determination of step 474 is repeated. If the determination of step 478 indicates that all points have been check in this way, a similar process is applied as points are traversed in the Y-direction of arrow 476. Similar comparisons with preceding points are made in step, with points selected to be Y-transition points being added to a Y-transition table in step 484, and with the point selection process continuing in step 486. If all of the points have been checked in this way, the step 468 is exited.

Figure 30:
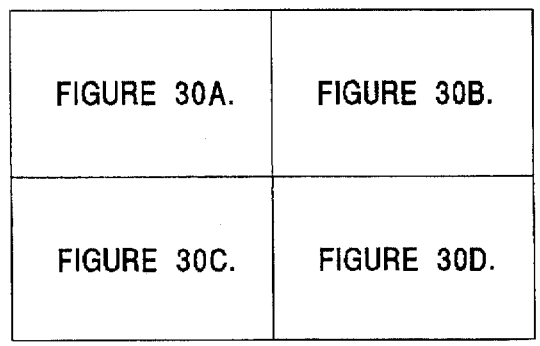
FIG. 30 is a flow diagram showing the formation of enclosures within the processes of FIG. 26, with FIG. 30A being an upper left portion of FIG. 30, with FIG. 30B being an upper right portion thereof, with FIG. 30C being a lower left portion thereof, and with FIG. 30D being a lower right portion thereof.
Figure 30A:
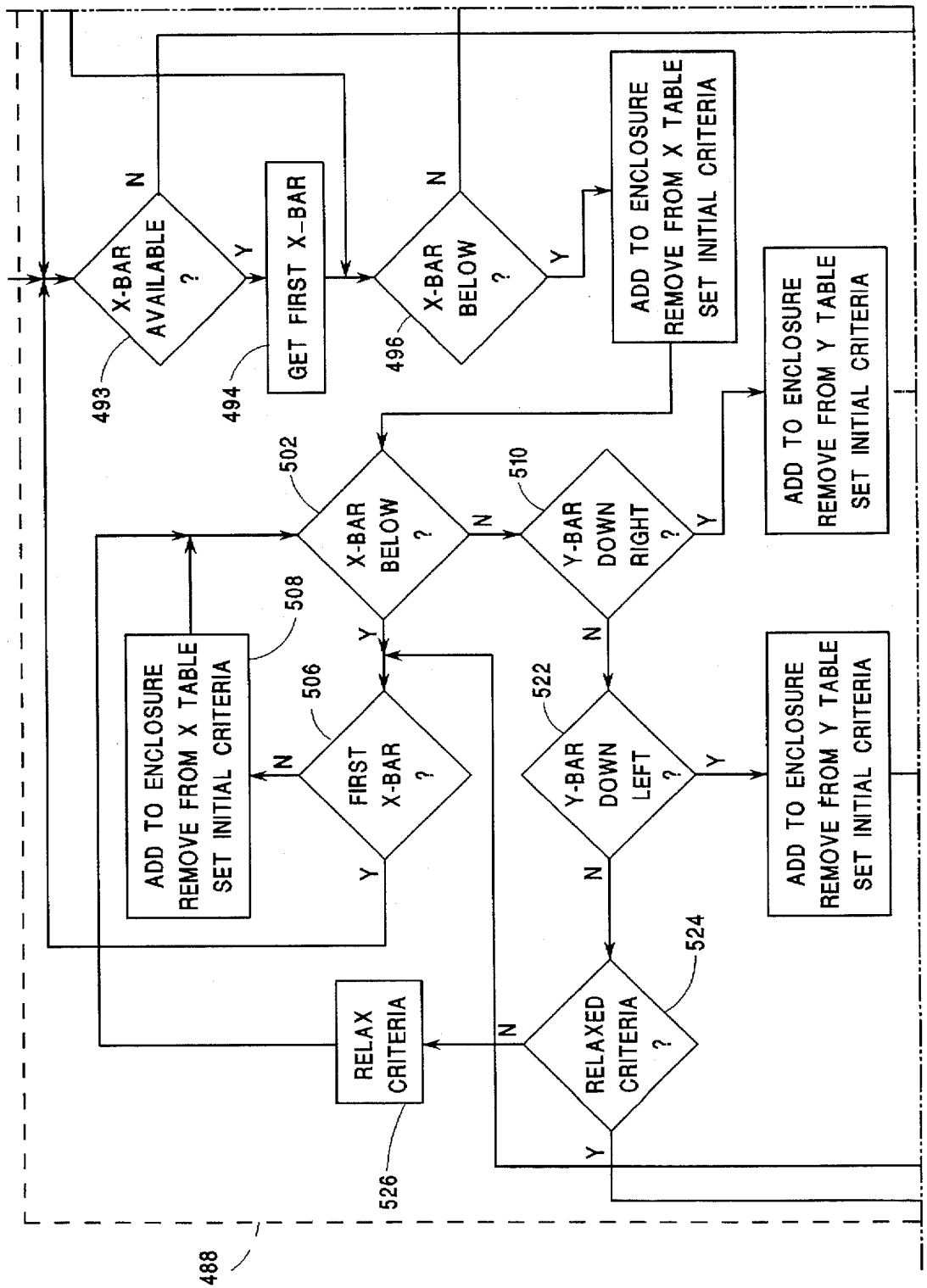
Figure 30B:
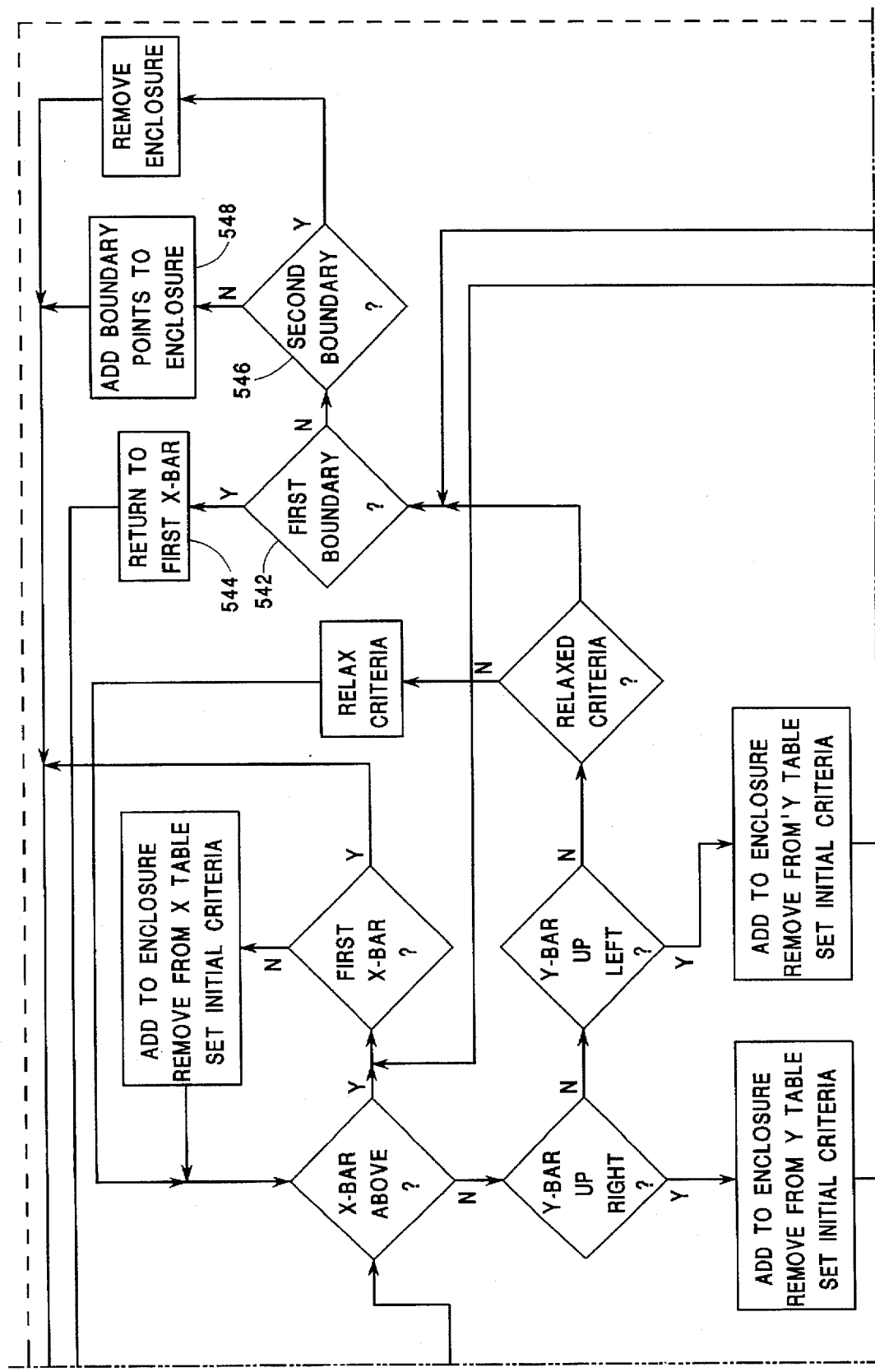
Figure 30C:
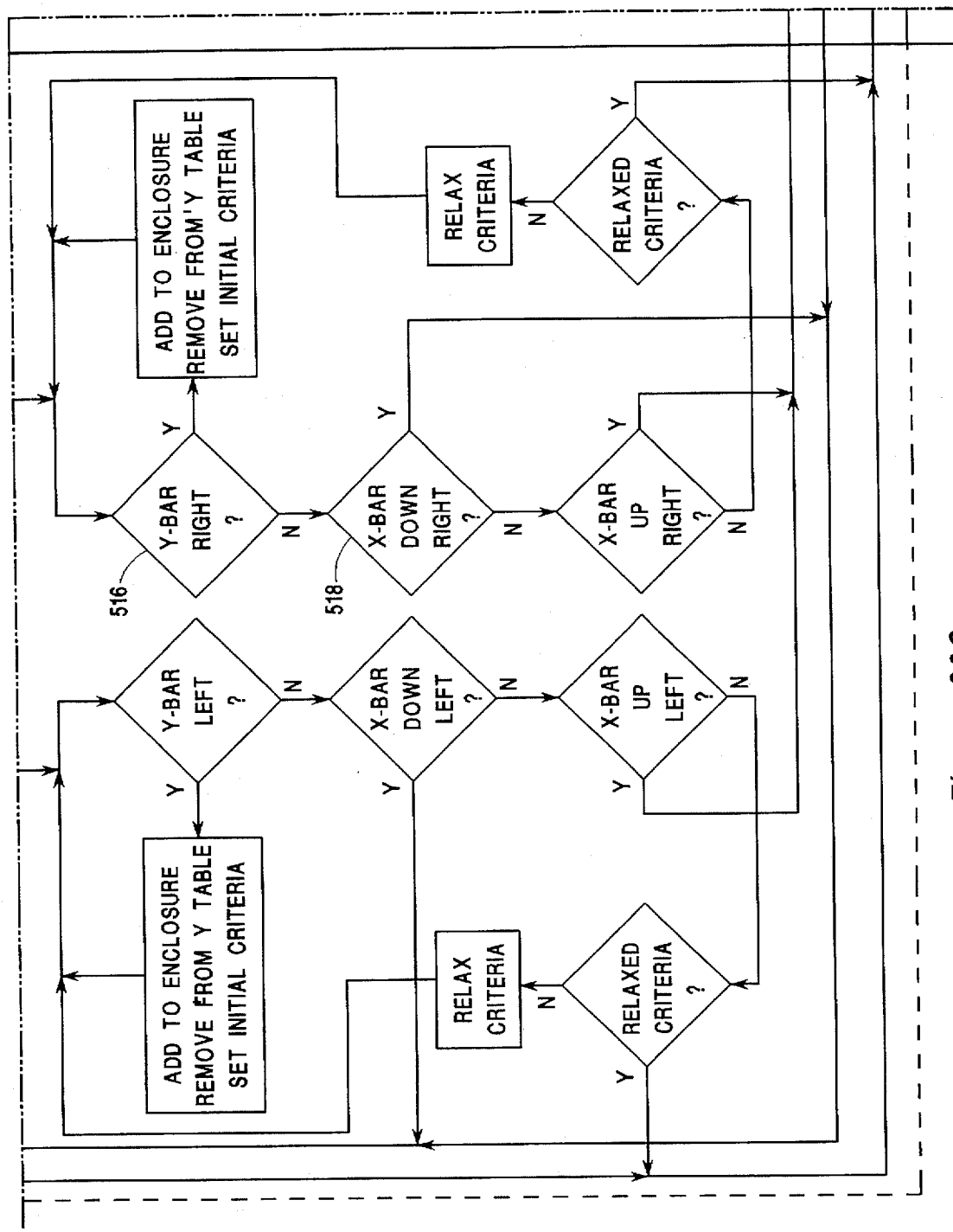
Figure 30D:
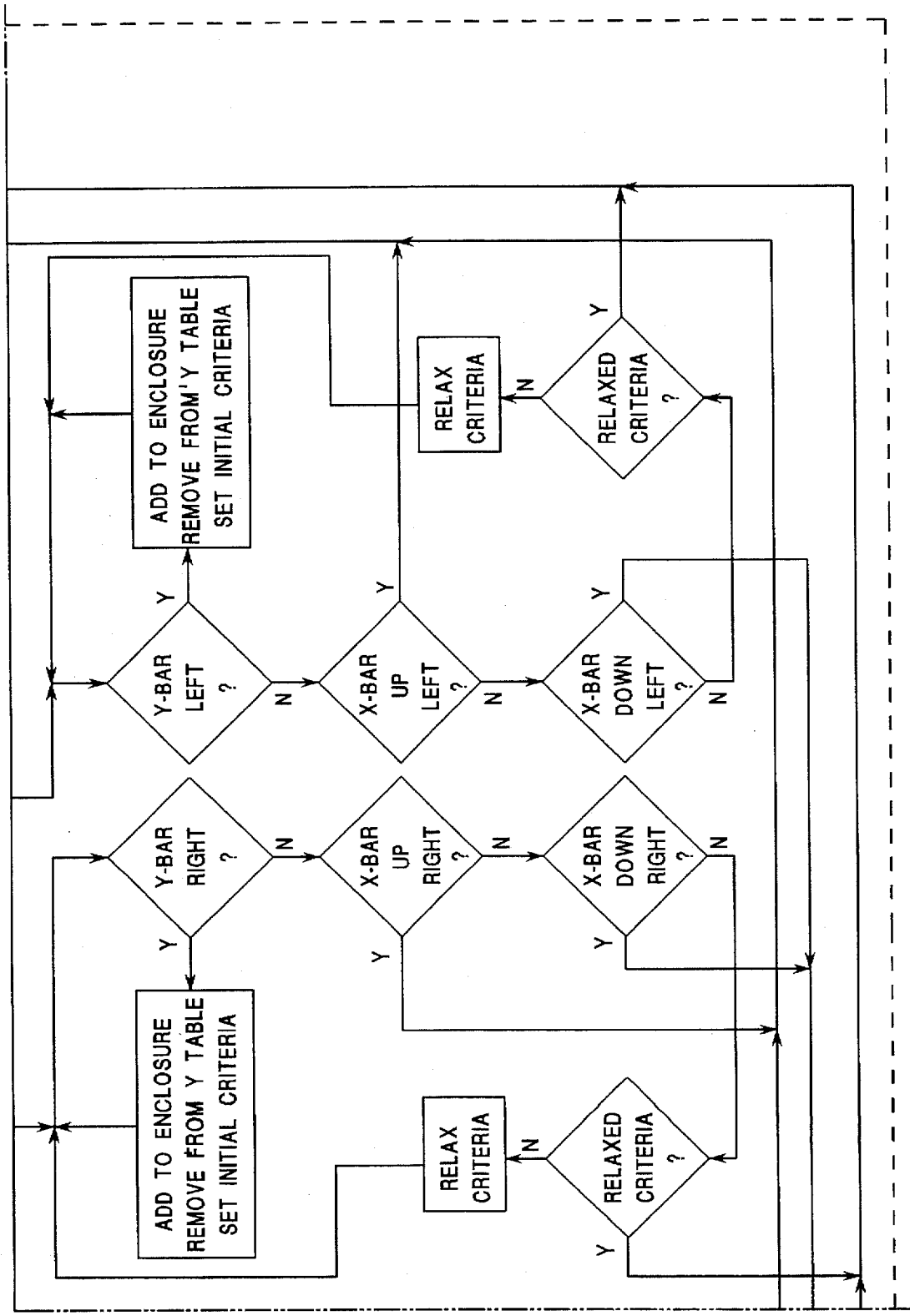

FIG. 30 is a flow diagram showing the processes which occur in step 488, in which enclosures are unwrapped. Referring again to FIG. 28, as well as to FIG. 30, in the following discussion, an X-transition pair 490 is called an X-bar, while a Y-transition pair 492 is called a Y-bar. In general, the process begins with the identification of a single X-bar, and proceeds as the pattern of X-bars and Y-bars is traversed to return to the beginning. A determination of whether an X-bar is available on the X-transition table is made in step 493. If it is, a first X-bar is chosen in step 494. For example, if X-bar 490 is chosen to be the first X-bar a determination is made that there is an X-bar 496 below it in step 498. Next, in step 500, the new X-bar 496 is added to the enclosure being developed while being removed from the X-transition table. Then, in step 502, it is determined that there is another X-bar 504 below the present X-bar 496. In step 506, it is determined that this is not the first X-bar 490, so the new X-bar 504 is added to the enclosure and removed from the X-transition table in step 508. Then, returning to step 502, it is determined that there is not an X-bar below. However, it is then determined in step 510 that there is a Y-bar 512 down and to the right. In step 514, this Y-bar 512 is added to the enclosure and removed from the Y-transition table. In step 516, it is determined that there is no Y-bar to the right of Y-bar 512, but in step 518, it is determined that there is an X-bar 520 down and to the right. Each time a new X-bar is found, a determination is made of whether it is the first X-bar, at which the enclosure has been started. If it is the first X-bar, the process of determining an enclosure has been completed, so it is ended. As each X-bar or Y-bar is added to the enclosure, it is removed from the X- or Y-transition table from which it has been selected, so it is impossible to continue backward along a line which is already part of the enclosure.

One situation which may be encountered is a gap in the enclosure of pixel heights defined by the equation given above. Such a gap may be caused, for example, by the effects of noise on the measurement made, or by the granularity of the pixel pattern, since each intensity value is, after all, an average level for a pixel. Therefore, a method is provided for dynamically adjusting the criteria used to determine transition points. For example, the requirement for a 100-nanometer change between adjacent pixels is changed to 50 nanometers. For example, if step 522 is reached, and if it is determined in this step that there is no Y-bar down and to the left, the process has reached an end of the enclosure, or, at least, a gap in the enclosure. It is next determined, in step 524, whether the criteria have already been relaxed. If they have not been relaxed, they are relaxed in step 526, and the process is returned to repeat the series of tests which have previously failed; in this example the process is returned to step 502. This relaxation of criteria is temporary. Whenever a point is found and added to the enclosure, the criteria are returned to their initial level. If step 524 is reached with the criteria in a relaxed state, the points representing the present enclosure are removed from the table of enclosure points in step 528. They will not be chosen again, since they have already been removed from the X- and Y-transition tables.

When a determination is made that a enclosure is complete, by determining that the first X-bar has been reached, for example in step 506, or when it is determined that a enclosure cannot be completed, for example in step 524, the process returns to step 493, to determine whether another X-bar is available. The changes in pixel height occurring across a single defect may be several times the quarter-wave length limit, causing several boundaries to be wrapped inside one another. Therefore, the process of looking for another enclosure is repeated until no X-bars remain in the X-transition table. At this point, which is determined by step 493, the process of forming enclosures in step 488 is exited.

Figure 31:
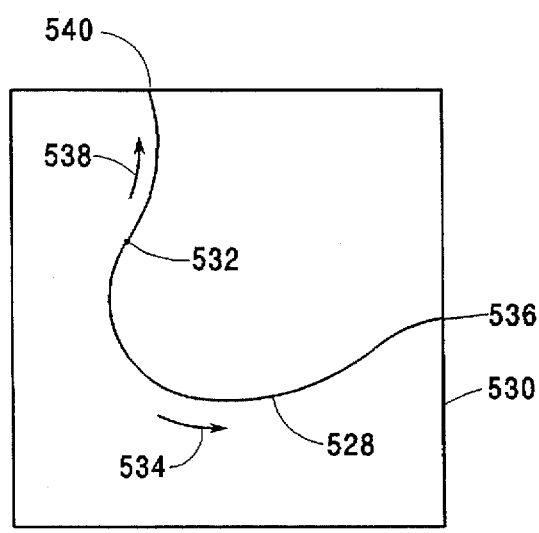
FIG. 31 is a schematic elevational view of an instance in which a defect extends beyond an area for which pixel heights can be determined.

FIG. 31 is a schematic elevational view of an instance in which a defect extends beyond the area for which pixel heights may be determined, causing an enclosure 528 to intersect a boundary 530 of the pixel area. In general, two ends of the enclosure intersect either one or two of the boundary surfaces. In the example of FIG. 30, the process of traversing the enclosure 528 begins with the selection of an X-bar at point 532, with the enclosure subsequently being traversed in the direction of arrow 534. When the intersection of the enclosure with the boundary at point 536 is found, the process returns to the first X-bar at point 532, to traverse the enclosure in the direction of arrow 538. When the intersection of the enclosure with the boundary at point 540 is found, the intervening boundary sections 544 and 546 are included as part of the enclosure. The determination of the portions boundary portions to make part of the enclosure is made by examining the direction at which the transitions occur at the portion of the enclosure intersecting the boundary, as indicated by the X and 0 symbols in FIG. 30.

Referring again to FIG. 30, when it is determined, for example, in block 524 that relaxed criteria have been applied, a determination is made in step 542 of whether a first boundary has been intersected. If it has been reached, the process is returned to the first X-bar of the present enclosure in step 544. From this point, the process of traversing the enclosure continues in the opposite direction, since points lying in the first direction chosen have been removed from the X and Y tables. When the next intersection with a boundary is found, as indicated in step 546, boundary points are added to the enclosure in step 548.

While the invention has been described in a preferred form or embodiment with some degree of particularity, it is understood that this description has been given only by way of example and that numerous changes in the details of construction, fabrication, and use, including the combination and arrangement of parts, may be made without departing from the spirit and scope of the invention.

What is claimed is:

1. Apparatus for determining characteristics of a test surface of a test specimen, wherein said apparatus comprises:

an instrument having an objective section for viewing said test surface, a first optical path directing a first image of said test surface at said objective section to a first sensing means for sensing features of said first image along an image receptive line, said first sensing means operating first output means to provide a first signal responsive to variations in said image, and a second optical path directing a second image of said test surface in said objective section to a second sensing means for sensing features of said second image extending within an area;

specimen drive means for driving said test specimen so that said test surface is moved past said objective section according to a preferred path of motion;

defect detection means for detecting variations in said first signal as said test specimen is driven to produce a flowing image on said first sensing means;

data storage means;

location sensing means providing location data describing movement of said test surface past said objective section;

first control means storing said location data within said data storage means in response to said defect detection means; and second control means operating said specimen drive means to move said test surface into locations corresponding to said location data stored within said data storage means, wherein said second control means moves said test surface successively between said locations, holding said test surface at said locations as a stationary image of said test surface is projected on said second sensing means.

2. The apparatus of claim 1:

wherein said instrument is an optical interferometer producing a flowing darkfield interferogram image at said first sensing means as said test surface is moved by said objective section, and producing a stationary interferogram image at said second sensing means as said test surface is held stationary at said objective section; and wherein a phase angle relationship between polarized beams creating said stationary interferogram is varied to determine spatial relationships among features of said test surface as a stationary image of said test surface is projected on said second sensing means.

3. The apparatus of claim 1:

wherein an adjustment within said instrument is varied as said test surface is moved past said objective section, with variations in said adjustment being responsive to changes in said test specimen;

wherein said instrument includes means for providing adjustment data responsive to variation of said adjustment in response to movement of said test specimen past said objective section;

wherein said first control means stores said adjustment data within said data storage means when said defect detection means detects said variation in said first signal; and wherein said second control means returns said adjustment to conditions referenced by said adjustment data stored within said data storage means when said test surface is moved successively between said locations to be held stationary as a stationary image of said test surface is projected on said second sensing means.

4. The apparatus of claim 3, wherein said instrument includes an objective lens within said objective section, and wherein said adjustment focusses said instrument by moving said objective lens along an optical path.

5. The apparatus of claim 4:

wherein said instrument is an optical interferometer producing a flowing interferogram image at said first sensing means;

wherein a phase angle relationship between polarized beams creating said flowing interferogram image is varied to maintain a darkfield interferogram image at said first sensing means;

wherein said apparatus instrument includes means for providing phase angle control data describing variations made to control said phase angle relationship; and wherein said first control means stores said phase angle control data within said data storage means when said defect detection means detects said variation in said first signal.

6. The apparatus of claim 5, wherein said instrument includes a Wollaston prism moved perpendicularly to said optical path to vary said phase angle relationship.

7. The apparatus of claim 2:

wherein said first sensing means includes a plurality of photosensitive elements extending in a line perpendicular to a direction of motion of said image caused by movement of said image as said test surface is moved past said objective section along said preferred path of motion; and wherein outputs of said photosensitive elements are sampled on a periodic basis, with an output of each said photosensitive element being responsive to an integrated sum of illumination received between sampling.

8. The apparatus of claim 7:

wherein said optical interferometer produces first and second lines of illumination on said test specimen, said first and second lines of illumination being separated in a direction along said preferred path of motion by a shearing distance; and wherein said test specimen is driven at a speed so that said test surface moves along said preferred path through an integral distance, which is a submultiple of said shearing distance, between times at which said photosensitive elements are sampled.

9. The apparatus of claim 8:

wherein said first control means includes means responsive to sequential operation of said defect detection means as a surface defect of said test surface moves past said first and second lines of illumination; and wherein said first control means stores said location data within said data storage means in response to operation of said defect detection means as said surface defect moves past said second line of illumination.

10. The apparatus of claim 9:

wherein said first control means includes means responsive to continued operation of said defect detection means as a large surface defect of said test surface, said large surface defect being longer in a direction along said preferred path of motion than said integral distance, moves by said objective section; and wherein said first control means stores said location data within said data storage means in response to a last operation of said defect detection means as said large surface defect moves by said objective section.

11. The apparatus of claim 7:

wherein said defect detection means provides an intensity level signal indicating an integrated illumination level received between sampling; and wherein said first control means stores said location data within said data storage means in response to operation of said defect detection means at sequential samples of said photosensitive elements.

12. The apparatus of claim 2:

wherein said second sensing means includes an area array of photosensitive elements, with each said photosensitive element providing a signal in response to the illumination of a pixel of said second image; and wherein said apparatus additionally comprises data processing means for determining a height of a segment of said test surface corresponding to each pixel of said second image.

13. The apparatus of claim 12, wherein said data processing means includes:

means for identifying transitional segment pairs, wherein a difference between said heights calculated for adjacent said segments exceeds a threshold level, and wherein said heights calculated for adjacent said segments place said segments on opposite sides of a plane corresponding to a dark image of said darkfield interferogram;

means for traversing adjacent said segment pairs to form an enclosure; and means for correcting said heights calculated for segments within said enclosure.

14. The apparatus of claim 13, wherein said means for identifying transitional segment pairs compares heights calculated for segments adjacent in a first direction and heights calculated for segments adjacent in a second direction, said second direction being perpendicular to said first direction.

15. The apparatus of claim 13, wherein said data processing means additionally includes:

means for identifying a failure to form said closed enclosure as an end of said enclosure is reached;

means for varying said threshold level to a lower value;

means for identifying an additional said transitional pair using said lower value; and means for restoring said threshold level.

16. The apparatus of claim 13, wherein said data processing means additionally includes:

means for identifying a first intersection of said enclosure with a first boundary location, beyond which segment height data is unavailable, as said enclosure is traversed in a first traverse direction;

means for identifying a second intersection of said enclosure with a second boundary location, beyond which segment height data is unavailable, as said enclosure is traversed in a direction opposite said first traverse direction; and means for including points extending, between said first boundary location and said second boundary location, along a boundary beyond which segment height data is unavailable, within said enclosure.

17. A process for determining characteristics of a test surface of a test specimen, wherein said process comprises:

moving said test specimen past an objective section of an instrument in a preferred direction, wherein said instrument includes a first optical path directing a first image of said test surface at said objective section to a first sensing means for sensing features of said image along an image receptive line, said first sensing means operating first output means to provide a first signal responsive to variations in said image, and a second optical path directing a second image of said test surface in said objective section to a second sensing means for sensing features of said image extending within an area, detecting variations in said first signal, and storing locations corresponding to said variations in said first signal within data storage means; and moving said test specimen among locations stored within said data storage means and holding said test surface at each said location as a stationary image of said test surface is projected on said second sensing means.

* * * * *